(12) United States Patent
Tokunaga et al.

(10) Patent No.: US 7,876,442 B2
(45) Date of Patent: Jan. 25, 2011

(54) ANALYZER

(75) Inventors: Kazutoshi Tokunaga, Kakogawa (JP); Norimasa Yamamoto, Kobe (JP)

(73) Assignee: Sysmex Corporation (JP)

( * ) Notice: Subject to any disclaimer, the term of this patent is extended or adjusted under 35 U.S.C. 154(b) by 189 days.

(21) Appl. No.: 12/005,694

(22) Filed: Dec. 27, 2007

(65) Prior Publication Data
US 2008/0158552 A1 Jul. 3, 2008

Related U.S. Application Data

(63) Continuation of application No. PCT/JP2006/312783, filed on Jun. 27, 2006.

(30) Foreign Application Priority Data

Jul. 1, 2005 (JP) .............................. 2005-193936

(51) Int. Cl.
*G01N 21/25* (2006.01)
(52) U.S. Cl. ..................................... 356/418
(58) Field of Classification Search ............. 356/72–73, 356/418
See application file for complete search history.

(56) References Cited

U.S. PATENT DOCUMENTS

| | | | | |
|---|---|---|---|---|
| 3,703,336 A | * | 11/1972 | Rosse et al. | .................... 356/39 |
| 4,082,464 A | * | 4/1978 | Johnson, Jr. | ................ 356/418 |
| 4,477,190 A | | 10/1984 | Liston et al. | |
| 2003/0072680 A1 | | 4/2003 | Higuchi et al. | |
| 2004/0078149 A1 | | 4/2004 | Matzinger | |

FOREIGN PATENT DOCUMENTS

| | | |
|---|---|---|
| CN | 1409102 A | 4/2003 |
| JP | 57-061922 A | 4/1982 |
| JP | 02-097297 A | 4/1990 |
| JP | 05-240782 A | 9/1993 |
| JP | 2003-083884 A | 3/2003 |
| JP | 2004-144750 A | 5/2004 |

OTHER PUBLICATIONS

International Search Report from International Application No. PCT/JP2006/312783 (3 pages).
Extended European Search Report dated Aug. 25, 2010 from corresponding European Application No. 06 76 7400.

* cited by examiner

*Primary Examiner*—Gregory J Toatley
*Assistant Examiner*—Abdullahi Nur
(74) *Attorney, Agent, or Firm*—Brinks Hofer Gilson & Lione

(57) ABSTRACT

An analyzer is provided with a light irradiation device. The light irradiation device includes a light source, and a rotatable filter section, which has a plurality of optical filters having different light transmission characteristics, and irradiates an analyzing object with light that passed through the optical filters arranged in a path of the light from the light source while the filter section is rotating, by successively switching the optical filters by rotating the filter section. The analyzer is also provided with an analyzing means for analyzing characteristics of the analyzing object, based on optical information obtained from the analyzing object irradiated with the light by the light irradiation device while the filter section is rotating.

22 Claims, 23 Drawing Sheets

| 48μsec STEP | CH (MUX NUMBER) | | |
|---|---|---|---|
| | LINE L0 | LINE L1 | LINE L2 |
| 0 | CH0(0) | CH16(0) | CH32(0) |
| 1 | CH0(0) | CH16(0) | CH32(0) |
| 2 | CH0(0) | CH16(0) | CH32(0) |
| 3 | CH1(1) | CH16(0) | CH32(0) |
| 4 | CH1(1) | CH17(1) | CH32(0) |
| 5 | CH1(1) | CH17(1) | CH33(1) |
| 6 | CH2(2) | CH17(1) | CH33(1) |
| 7 | CH2(2) | CH18(2) | CH33(1) |
| ⋮ | ⋮ | ⋮ | ⋮ |
| 44 | CH14(14) | CH30(14) | CH46(14) |
| 45 | CH15(15) | CH30(14) | CH46(14) |
| 46 | CH15(15) | CH31(15) | CH46(14) |
| 47 | CH15(15) | CH31(15) | CH47(15) |
| 48 | CH0(0) | CH31(15) | CH47(15) |
| 49 | CH0(0) | CH16(0) | CH47(15) |
| 50 | CH0(0) | CH16(0) | CH32(0) |

▨ MULTIPLEXER SWITCHING + NORMALIZATION + AMPLIFICATION
☐ SIGNAL WAIT PROCESSING
▧ A-D CONVERSION + DATA STORAGE

ANALYZER

CROSS-REFERENCE TO RELATED APPLICATIONS

The priority application number JP2005-193936, Analyzer, Jul. 1, 2005, Kazutoshi Tokunaga and Norimasa Yamamoto, upon which this patent application is based is hereby incorporated by reference. This application is a continuation of PCT/JP2006/312783, Analyzer, Jun. 27, 2006, Kazutoshi Tokunaga and Norimasa Yamamoto.

BACKGROUND OF THE INVENTION

1. Field of the Invention

The present invention relates to an analyzer, and more particularly, it relates to an analyzer comprising a light irradiation device switching optical filters arranged on a path of light from a light source and irradiating an analyzing object with lights transmitted through the optical filters.

2. Description of the Background Art

In general, an analyzer comprising a light irradiation device switching optical filters arranged on a path of light from a light source in accordance with characteristics of reagents employed for analyses and methods of analyses and irradiating an analyzing object with light having prescribed wavelength characteristics is known as an optical analyzer employed for biochemical tests, blood coagulation tests or the like (Japanese Patent Laying-Open No. 2003-83884, for example). The conventional analyzer disclosed in the aforementioned Japanese Patent Laying-Open No. 2003-83884 is so formed as to switch the wavelength characteristics of the light applied to the analyzing object through the optical filters from the light source by rotating a rotating plate on which a plurality of the optical filters having different light transmission characteristics respectively are set and switching the optical filters arranged on the path of the light from the light source. In the analyzer disclosed in the aforementioned Japanese Patent Laying-Open No. 2003-83884, when the analyzing object is analyzed by irradiating the analyzing object with the light, the analyzing object is analyzed by stopping the optical filter having desired light transmission characteristics at the path of the light from the light source and irradiating the analyzing object with the light having prescribed wavelength characteristics transmitting through the optical filter.

In the conventional analyzer disclosed in aforementioned Japanese Patent Laying-Open No. 2003-83884, however, when the analyzing object is analyzed by irradiating the analyzing object with the light, the optical filter is stopped on the path of the light from the light source and thereafter the analyzing object is irradiated with the light transmitting through the optical filter. In other words, the analysis of the analyzing object is merely performed with the light having specific wavelength characteristics at a prescribed time (temporal point). In some analyses, an optical analysis must be performed continuously or frequently at short intervals not only at the prescribed time. In an analysis of blood coagulation time, for example, light must be applied continuously or intermittently at short intervals of one second or less. Another analysis must be performed by applying a plurality of types of lights having specific wavelength characteristics. In this case, if analyzing a reacted sample, light having first specific wavelength characteristics and light having second specific wavelength characteristics are desired to be applied substantially at the same time.

In the conventional analyzer, however, the rotating plate must be repeatedly rotated and stopped and hence the optical filters are disadvantageously difficult to be switched frequently in a short period. When the optical filters are switched, the rotating plate must be repeatedly rotated and stopped, which disadvantageously complicates control of the rotating plate. The optical filter must be correctly stopped on the path of the light from the light source, and hence an expensive motor having a high positioning accuracy must be employed and positioning of the optical filter with respect to the path of the light from the light source is required.

SUMMARY OF THE INVENTION

The present invention has been proposed in order to solve the aforementioned problem, and an object of the present invention is to provide an analyzer at a cost lower than a conventional one, capable of switching optical filters frequently in a short period and requiring no positioning of the optical filters while inhibiting control of switching the optical filters from complication.

In order to attain the aforementioned object, an analyzer according to a first aspect of the present invention comprises a light irradiation device including a light source and a rotatable filter section having a plurality of optical filters with different light transmission characteristics respectively and irradiating an analyzing object with lights transmitted through the optical filters during rotation of the filter section while successively switching the optical filters arranged on a path of a light from the light source by rotating the filter section, and analytic means analyzing characteristics of the analyzing object on the basis of optical information obtained from the analyzing object irradiated with the lights by the light irradiation device during the rotation of the filter section.

An analyzer according to a second aspect of the present invention comprises a light source, a plurality of optical filters having different light transmission characteristics respectively, filter moving means moving the plurality of optical filters such that the plurality of optical filters successively pass through a path of a light from the light source at a constant speed, and analytic means analyzing characteristics of the analyzing object on the basis of optical information obtained by irradiating an analyzing object with lights transmitted through the optical filters from the light source.

An analyzer according to a third aspect of the present invention comprises a light irradiation device including a light source and a rotatable filter section having a plurality of optical filters with different light transmission characteristics respectively and irradiating an analyzing object with lights transmitted through the optical filters while successively switching the optical filters arranged on a path of a light from the light source at a time interval of at most one second by rotating the filter section, and analytic means analyzing characteristics of the analyzing object on the basis of optical information obtained from the analyzing object irradiated with the lights by the light irradiation device.

DESCRIPTION OF THE PREFERRED EMBODIMENTS

Embodiments of the present invention are hereinafter described with reference to the drawings.

First Embodiment

The structure of an analytic system 1 according to a first embodiment of the present invention is described with reference to FIGS. 1 to 12.

The analytic system 1 according to the first embodiment of the present invention is a system for optically measuring and analyzing the quantities and the degrees of activity of specific substances related to a blood coagulative/fibrinolytic function, employing blood plasma as a specimen. The analytic system 1 according to the first embodiment optically measures the specimen with a coagulation time method. The coagulation time method employed in the first embodiment is a measuring method detecting the process of coagulation of the specimen as change of transmitted light.

Figure 25:
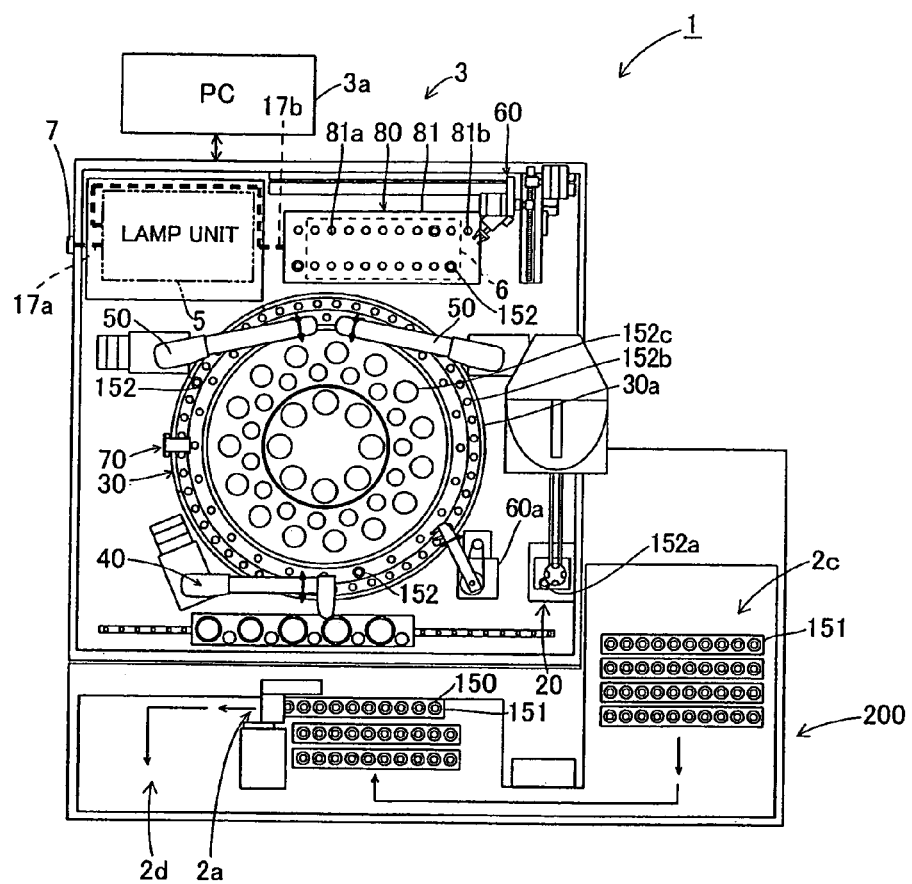
[FIG. 25] A plan view showing the overall structure of the analytic system including no extension analyzer according to the first embodiment of the present invention.

The structure of the analytic system 1 can be varied with the scale of an institution where the system 1 is installed. When installed in an institution having a relatively small number of specimens, for example, the analytic system 1 is constituted of an analyzer 3 and a transporter 200 for supplying specimens to the analyzer 3, as shown in FIG. 25. When installed in an institution having a large number of specimens, on the other hand, an extension analyzer 4 is added to the analytic system 1 and a transporter 2 substitutes for the transporter 200, so that the analytic system 1 is constituted of a transporter transport mechanism section 2, an analyzer 3 and an extension analyzer 4. Thus, the extension analyzer 4 added to the analytic system 1 extends the specimen throughput of the analytic system 1.

Figure 1:
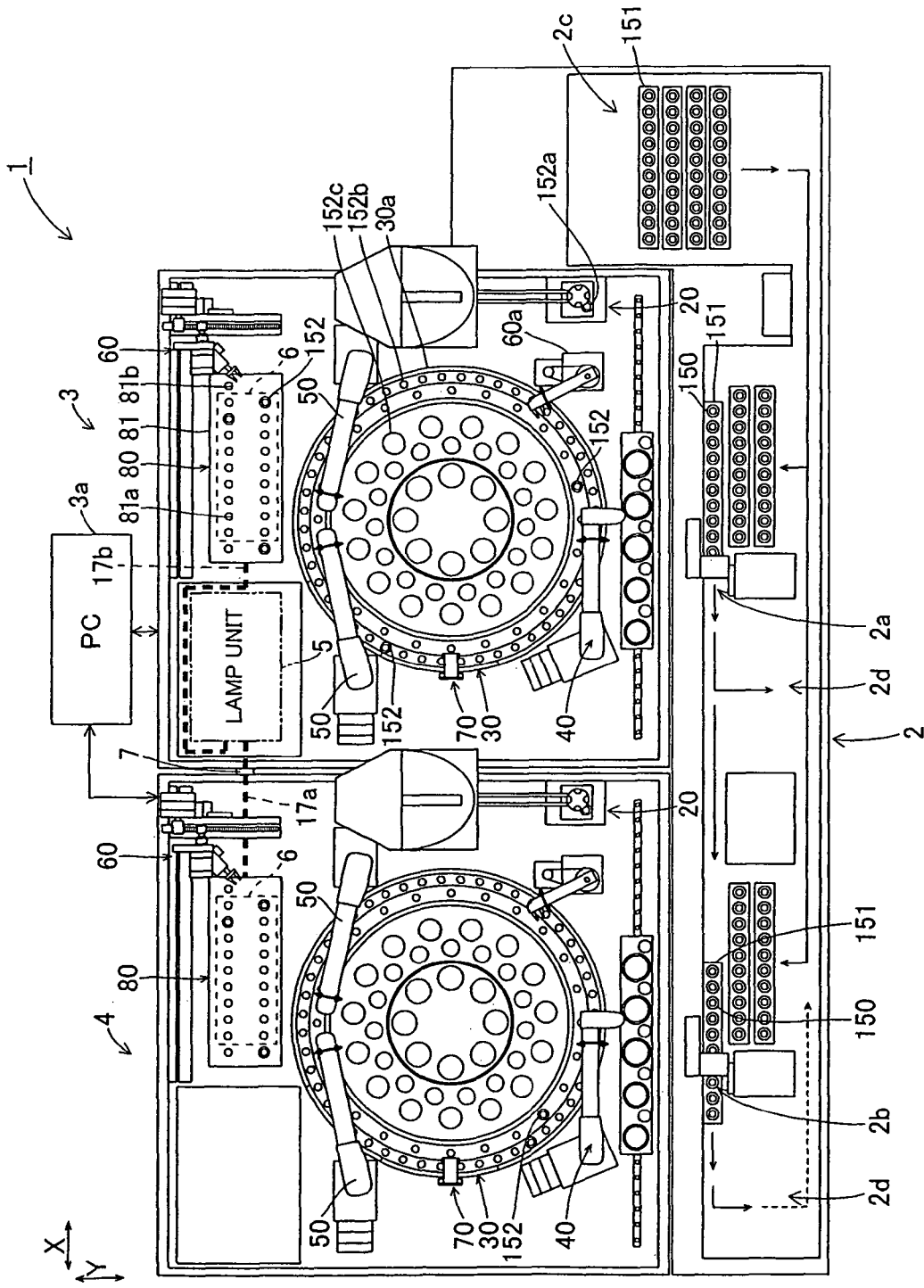
[FIG. 1] A plan view showing the overall structure of an analytic system including an analyzer and an extension analyzer according to a first embodiment of the present invention.

The transport mechanism section 2 shown in FIG. 1 has a function of transporting racks 151 each carrying a plurality of (10 in this embodiment) test tubes 150 storing specimens to suctional positions 2a and 2b (see FIG. 1) of the analyzer 3 and the extension analyzer 4 respectively, in order to supply the specimens to the analyzer 3 and the extension analyzer 4. This transport mechanism section 2 has a rack set area 2c for setting racks 151 carrying test tubes 150 storing untreated specimens and a rack storage area 2d for storing racks 151 carrying test tubes 150 storing treated specimens.

The analyzer 3 and the extension analyzer 4 are so formed as to optically measure different specimens supplied from the transport mechanism section 2 thereby acquiring optical information related to the supplied specimens respectively. According to the first embodiment, the analyzer 3 and the extension analyzer 4 optically measure specimens injected into cuvettes 152 (see FIG. 1) from the test tubes 150 located on the transport mechanism section 2 respectively. The analyzer 3 includes an information processing terminal 3a, a lamp unit 5 and a control board 6. The analyzer 3 further includes a cuvette supply section 20, a rotary transport section 30, a specimen injection arm 40, two reagent injection arms 50, cuvette transfer sections 60 and 60a, a first optical information acquisition section 70 and a second optical information acquisition section 80. The extension analyzer 4 also includes a control board 6, a cuvette supply section 20, a rotary transport section 30, a specimen injection arm 40, two reagent injection arms 50, cuvette transfer section 60, a first optical information acquisition section 70 and a second optical information acquisition section 80 identical to those provided on the analyzer 3. These components are identically arranged in the analyzer 3 and the extension analyzer 4.

According to the first embodiment, only the analyzer 3 includes the information processing terminal 3a and the lamp unit 5, while the extension analyzer 4 includes no such components.

Figure 2:
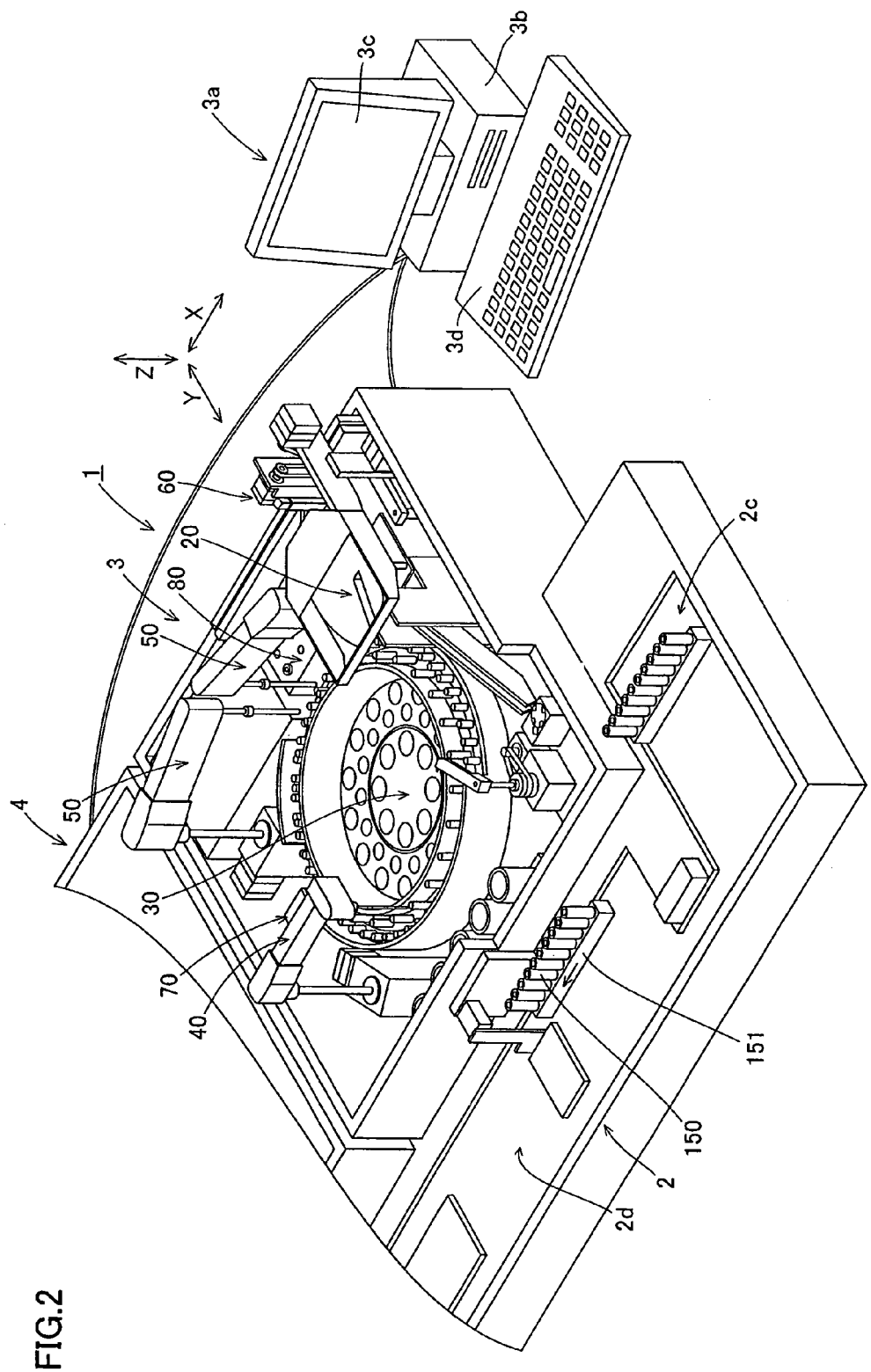
[FIG. 2] A perspective view partially showing the analytic system including the analyzer and the extension analyzer according to the first embodiment shown in FIG. 1.

The information processing terminal 3a is electrically connected not only to the body of the analyzer 3 but also to the extension analyzer 4 through communication cables. In other words, the analyzer 3 and the extension analyzer 4 share the information processing terminal 3a of the analyzer 3 in common. The analyzer 3 and the extension analyzer 4 have functions of transmitting optical information acquired from specimens to the information processing terminal 3a. The information processing terminal 3a is formed by a personal computer (PC), and includes a PC body 3b, a display section 3c and a keyboard 3d, as shown in FIG. 2. The PC body 3b has a function of analyzing the characteristics of specimens (measurement samples) on the basis of signals (optical information) acquired by signal processing sections 111 and control sections 112, described later, of the control boards 6 when the lamp unit 5 irradiates the specimens with lights having prescribed wavelength characteristics. According to the first embodiment, the PC body 3b of the information processing terminal 3a is so formed as to analyze times (coagulation times) required for the specimens to reach prescribed coagulation states from prescribed timing after reagents are mixed into the specimens. The PC body 3b includes a control section (not shown) formed by a CPU, a ROM, a RAM, a hard disk etc. The display section 3c is provided for displaying information such as results of analysis obtained in the PC body 3b. As hereinabove described, the analyzer 3 and the extension analyzer 4 are identical in structure to each other except that the extension analyzer 4 includes neither information processing terminal 3a nor lamp unit 5. Therefore, the structure of the analyzer 3 is described in the following.

Figure 3:
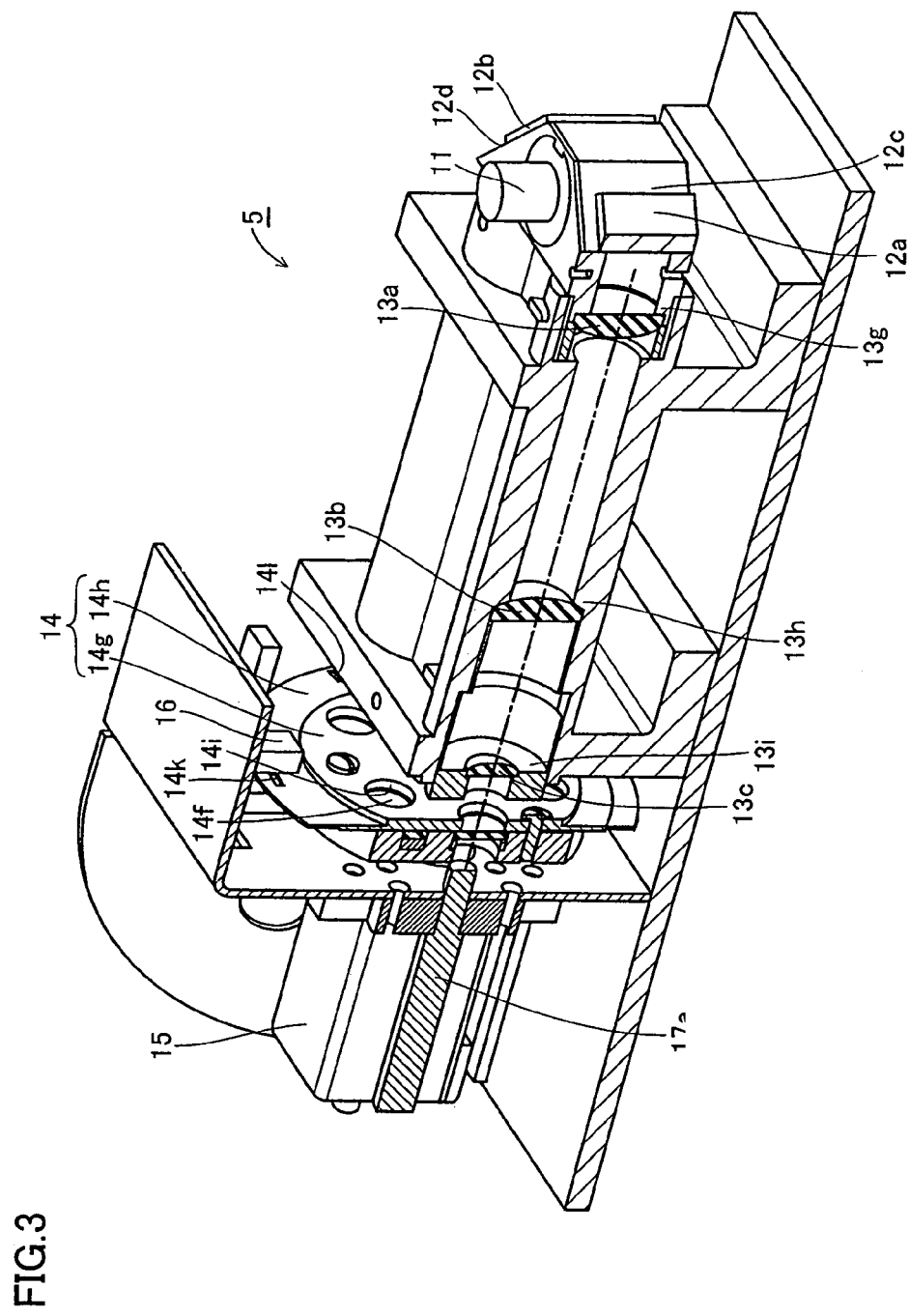
[FIG. 3] A perspective view for illustrating the structure of a lamp unit included in the analyzer according to the first embodiment shown in FIG. 1.
Figure 4:
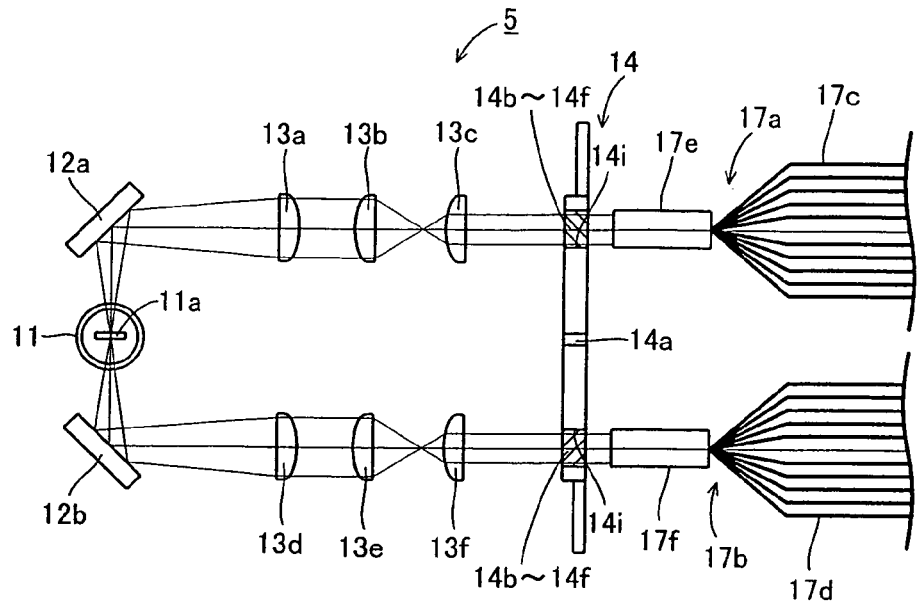
[FIG. 4] A schematic diagram showing the structure of the lamp unit included in the analyzer according to the first embodiment shown in FIG. 3.

As shown in FIGS. 3 and 4, the lamp unit 5 has a halogen lamp 11 serving as a light source, two mirrors 12a and 12b, two sets of condensing lenses 13a to 13c and 13d to 13f, a discoidal filter section 14, a motor 15, a light transmission sensor 16 and two optical fiber members 17a and 17b. In this lamp unit 5, the halogen lamp 11, the mirror 12b, the condensing lenses 13d to 13f and the optical fiber member 17b constitute an optical system for the analyzer 3, while the halogen lamp 11, the mirror 12a, the condensing lenses 13a to 13c and the optical fiber member 17a constitute an optical system for the extension analyzer 4.

The forward end of the optical fiber member 17b is connected to the second optical information acquisition section 80 of the analyzer 3. The forward end of the optical fiber member 17a is connected to the second optical information acquisition section 80 of the extension analyzer 4 only when the extension analyzer 4 is provided on the analytic system 1.

The mirror 12a, the condensing lenses 13a to 13c and the optical fiber member 17a may not be provided on the lamp unit 5 when the extension analyzer 4 is not provided on the analytic system 1. The mirror 12a and the condensing lenses 13a to 13c may be mounted on a mirror mounting section 12c and lens mounting sections 13g to 13i respectively when the extension analyzer 4 is added to the analytic system 1. Thus, the cost for the lamp unit 5 can be reduced when the extension analyzer 4 is not provided on the analytic system 1.

The optical fiber members 17a and 17b are constituted of 21 optical fibers 17c and 21 optical fibers 17d respectively. Bundling members 17e and 17f bundle the 21 optical fibers 17c and the 21 optical fibers 17d respectively. The halogen lamp 11 includes a platelike filament 11a capable of emitting lights from both surfaces, as shown in FIG. 4. Thus, the halogen lamp 11 is so formed as to emit lights of the same characteristics from both surfaces of the platelike filament 11a. The platelike filament, having small dispersion in the quantity of light in a photoirradiation region thereof, is so employed as to stabilize the quantities of lights (transmitted lights or scattered lights) obtained by irradiating measurement samples with lights, thereby suppressing measurement errors. The two mirrors 12a and 12b are provided for reflecting the lights emitted from the halogen lamp 11 and guiding the same to prescribed optical paths respectively. In other words, the mirrors 12a and 12b are arranged on both sides of the filament 11a, and located on positions correctly opposed to first and second surfaces of the filament 11a respectively. Further, the mirrors 12a and 12b are inclined with respect to the filament 11a, in order to change the traveling directions of the lights emitted from the filament 11a by 90° respectively.

The mirror 12a reflects the light emitted from the first surface of the platelike filament 11a of the halogen lamp 11, while the mirror 12b reflects the light emitted from the second surface of the platelike filament 11a. Thus, the lights reflected by the mirrors 12a and 12b form two optical paths. The mirrors 12a and 12b are detachably mounted on the mirror mounting sections 12c and 12d respectively, as shown in FIG. 3. The condensing lenses 13a, 13c and 13d are arranged on the path of the light whose traveling direction is changed by the mirror 12a in this order from the side closer to the mirror 12a, as shown in FIG. 4. Similarly to the condensing lenses 13a to 13c, the condensing lenses 13d to 13f are arranged on the path of the light whose traveling direction is changed by the mirror 12b in this order from the side closer to the mirror 12b. The two sets of condensing lenses 13a to 13c and 13d to 13f are so arranged that the directions of arrangement thereof are parallel to each other.

As shown in FIG. 4, the two sets of condensing lenses 13a to 13c and 13d to 13f condense the two lights reflected by the mirrors 12a and 12b for guiding the same to the optical fiber members 17a and 17b respectively, as shown in FIG. 4. The two lights reflected by the mirrors 12a and 12b are condensed by the condensing lenses 13a to 13c and 13d to 13f respectively, transmitted through any ones of optical filters 14b to 14f and guided to the optical fiber members 17a and 17b respectively. The condensing lenses 13a to 13c are detachably mounted on the lens mounting sections 13g to 13i respectively, as shown in FIG. 3. The condensing lenses 13d to 13f are also detachably mounted on corresponding lens mounting sections (not shown) respectively.

Figure 5:
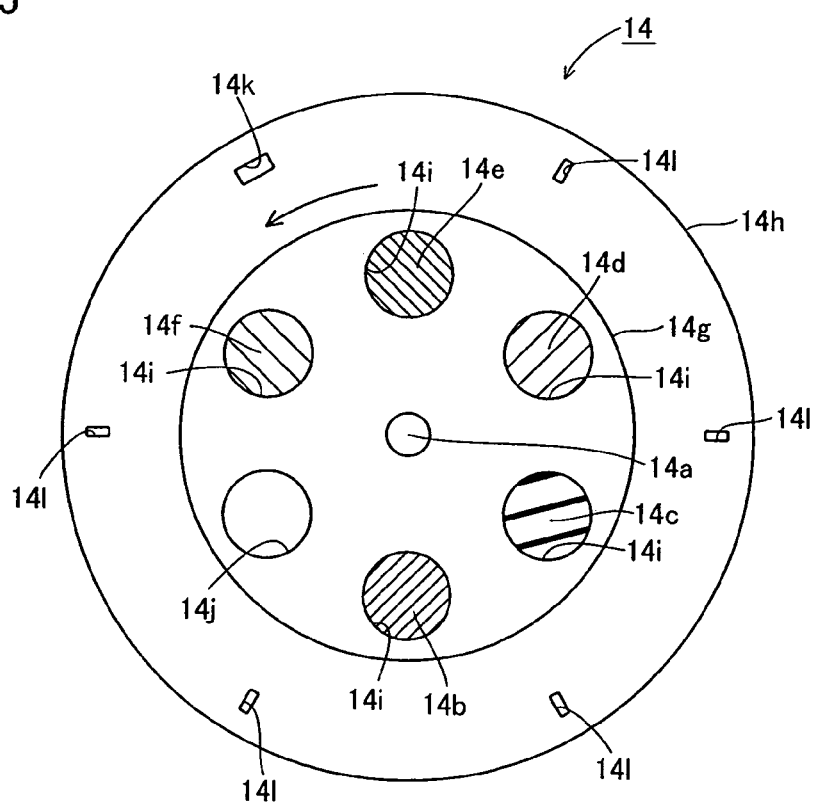
[FIG. 5] A plan view showing a filter section of the lamp unit included in the analyzer according to the first embodiment shown in FIG. 3.

According to the first embodiment, the filter section 14 of the lamp unit 5 is provided to be rotatable about a shaft 14a, as shown in FIG. 5. This filter section 14 is constituted of a filter plate 14g provided with five optical filters 14b to 14f having different light transmission characteristics (transmission wavelengths) and a filter plate holding member 14h holding the filter plate 14g to expose both surfaces of the optical filters 14b to 14f. The filter plate 14g is fixed to the filter plate holding member 14h. This filter plate 14g is provided with five holes 14i for receiving the optical filters 14b to 14f respectively. The five optical filters 14b, 14c, 14d, 14e and 14f having different light transmission characteristics (transmission wavelengths) are set in the five holes 14i respectively. The filter plate 14g is further provided with a hole 14j. The hole 14j is blocked not to transmit light. The holes 14i and 14j are provided at a prescribed angular interval (regular interval of 60° according to the first embodiment) along the direction of rotation of the filter section 14. The hole 14j is a preliminary hole for receiving an additional filter when the analytic system 1 requires this filter.

The optical filters 14b, 14c, 14d, 14e and 14f transmit lights having wavelengths of 340 nm, 405 nm, 575 nm, 660 nm and 800 nm respectively, while transmitting no lights of other wavelengths. Therefore, lights transmitted through the optical filters 14b, 14c, 14d, 14e and 14f have wavelength characteristics of 340 nm, 405 nm, 575 nm, 660 nm and 800 nm respectively.

The filter plate holding member 14h is so annularly formed that the filter plate 14g is arranged on a central hole section thereof. The filter plate holding member 14h is circumferentially provided with six slits at a regular interval (60°). One of the six slits is an origin slit 14k having a larger width than the remaining five slits 14l along the direction of rotation of the filter plate holding member 14h.

The origin slit 14k and the normal slits 14l are formed on intermediate angular positions (deviating from the holes 14i and 14j by 30°) between the adjacent holes 14i and 14j at the regular interval of 60°. The motor 15 (see FIG. 3) is connected to the shaft 14a of the filter section 14. Thus, the motor 15 drives the filter section 14 to rotate about the shaft 14a.

According to the first embodiment, the control board 6 (see FIG. 1) controls the motor 15 to rotate the filter section 14 at a substantially constant speed when the lamp unit 5 emits a light transmitted through any of the optical filters 14b to 14f. Following this rotation of the filter section 14, the five optical filters 14b to 14f having different light transmission characteristics and the blocked hole 14j (see FIG. 5) are intermittently successively arranged on paths of the lights condensed by the condensing lenses 13a to 13c (see FIG. 4) and the condensing lenses 13d to 13f (see FIG. 4) respectively. Thus, the lamp unit 5 intermittently successively applies five types of lights having different wavelength characteristics.

The light transmission sensor 16 is provided for detecting passage of the origin slit 14k and the normal slits 14l following the rotation of the filter section 14, as shown in FIG. 3. In other words, the sensor 16 is so set as to hold the filter section 14 between a light source and a photoreceptive section. This sensor 16 is provided in correspondence to a position passed by the origin slit 14k and the normal slits 14l.

Upon passage of the origin slit 14k and the normal slits 14l, therefore, the photoreceptive section detects light from the light source through the slits so that the sensor 16 outputs detection signals. Since the origin slit 14k is larger in width than the normal slits 14l, the detection signal output from the sensor 16 upon passage of the origin slit 14k has a longer output period than the detection signals output from the sensor 16 upon passage of the normal slits 14l. The detection signals output from the sensor 16 are transmitted to the control board 6 (see FIG. 1), so that a filter rotation monitoring section 112b, described later, of the control board 6 monitors whether or not the filter section 14 normally rotates on the basis of the detection signals received from the sensor 16.

The two optical fiber members 17a and 17b are provided for guiding the lights received from the lamp unit 5 to measurement samples stored in the cuvettes 152 set on the second optical information acquisition sections 80 of the analyzer 3 and the extension analyzer 4 respectively. As shown in FIG. 1, the optical fiber member 17a is so set as to extend from the lamp unit 5 toward the second optical information acquisition section 80 of the extension analyzer 4 through an extension connecting terminal 7 provided on the extension analyzer 4. Also the optical fiber member 17b is so set as to extend from the lamp unit 5 toward the second optical information acquisition section 80 of the analyzer 3. Thus, the single lamp unit 5 can supply lights to the second optical information acquisition sections 80 of the analyzer 3 and the extension analyzer 4 respectively.

As shown in FIG. 4, each of the optical fiber members 17a and 17b is so formed as to receive a light transmitted through any of the optical filters 14b to 14f from an end bundled by the bundling member 17e (17f). The 21 optical fibers 17c are so arranged as to supply lights to 20 receiving holes 81a and a reference light measurement hole 81b, described later, of the second optical information acquisition section 80 of the extension analyzer 4 (see FIG. 1) respectively. Also the 21 optical fiber members 17d are so arranged as to supply lights to 20 receiving holes 81a and a reference light measurement hole 81b, described later, of the second optical information acquisition section 80 of the analyzer 3 (see FIG. 1) respectively.

The cuvette supply section 20 arranges the plurality of cuvettes 152, randomly introduced by a user, one by one on a position 152a. The cuvette transfer section 60a transfers the cuvettes 152, each arranged on the position 152a, one by one to the rotary transport section 30. The rotary transport section 30 includes a discoidal table 30a, which is provided with a plurality of holes 152b for storing the cuvettes 152 and a plurality of holes 152c for storing reagent vessels (not shown) storing reagents added to specimens stored in the cuvettes 152. The rotary transport section 30 transports the cuvettes 152 and the reagent vessels by rotating the table 30a.

The specimen injection arm 40 has a function of sucking specimens from the test tubes 150 transported to the sectional/injective position 2a (2b) by the transport mechanism section 2 while injecting the sucked specimens into the cuvettes 152 transferred by the rotary transport section 30. The reagent injection arms 50 are provided for injecting the reagents stored in the reagent vessels (not shown) placed on the rotary transport section 30 into the cuvettes 152 held on the rotary transport section 30 thereby mixing the reagents into the specimens stored in the cuvettes 152. The cuvette transfer section 60 is provided for transferring the cuvettes 152 between the rotary transport section 30 and a cuvette receiving section 81, described later, of the second optical information acquisition section 80.

Figure 6:
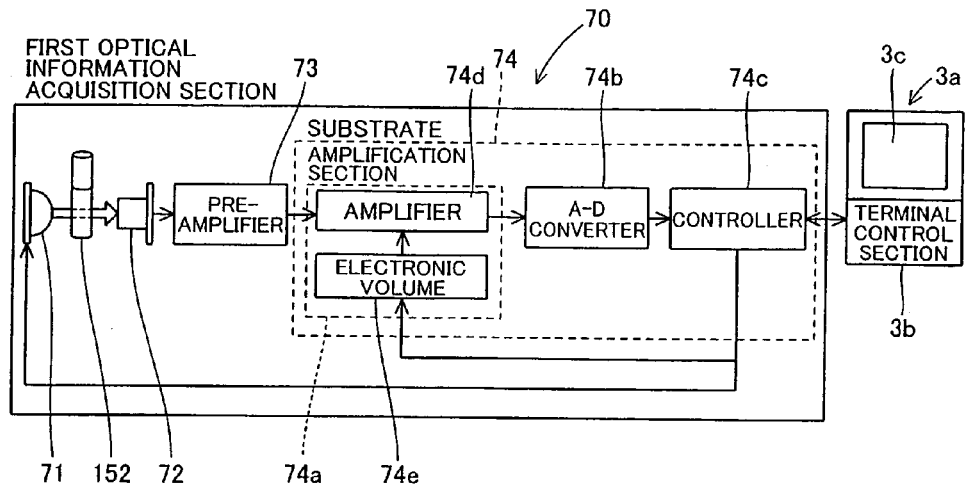
[FIG. 6] A block diagram for illustrating the structure of a first optical information acquisition section of the analyzer according to the first embodiment shown in FIG. 1.

The first optical information acquisition section 70 is so formed as to acquire optical information from the specimens, in order to detect presence/absence, types and contents of interference substances (hemoglobin, chyle (lipid) and bilirubin) in the specimens not yet mixed with the reagents. The first optical information acquisition section 70 acquires the optical information before the second optical information acquisition section 80 optically measures the specimens. As shown in FIG. 6, the first optical information acquisition section 70 includes a light-emitting diode (LED) 71 serving as a light source, a photoelectric conversion element 72, a preamplifier 73 and a substrate 74. This first optical information acquisition section 70 acquires the optical information from the specimens by irradiating the cuvettes 152 held on the rotary transport section 30 with lights, described below.

The light-emitting diode 71 is so provided as to irradiate the cuvettes 152 held on the rotary transport section 30 with lights. A controller 74c of the substrate 74 (see FIG. 6) controls the light-emitting diode 71 to periodically successively emit lights having three types of wavelength characteristics. More specifically, the light-emitting diode 71 periodically successively emits blue, green and red lights having wavelength characteristics of 430 nm, 565 nm and 627 nm respectively. The photoelectric conversion element 72 has a function of detecting the lights emitted from the light-emitting diode 71 and transmitted through the cuvettes 152 and converting the same to electric signals. The preamplifier 73 is provided for amplifying the electric signals received from the photoelectric conversion element 72.

The substrate 74 has a function of amplifying and digitizing the electric signals received from the photoelectric conversion element 72 and transmitting the same to the PC body 3b of the information processing terminal 3a. This substrate 74 is provided with an amplification section 74a, an A-D converter 74b and a controller 74c, as shown in FIG. 6. The amplification section 74a has an amplifier 74d and an electronic volume 74e. The amplifier 74d is provided for amplifying the electric signals received from the preamplifier 73. The amplifier 74d is so formed as to input a control signal from the controller 74c into the electronic volume 74e thereby controlling the gain (amplification factor) of the amplifier 74d. The A-D converter 74b is provided for converting the electric signals (analog signals) amplified by the amplifier 74d to digital signals.

The controller 74c is so formed as to change the gain (amplification factor) of the amplifier 74d in response to periodic change of the wavelength characteristics (430 nm, 565 nm and 627 nm) of the lights emitted from the light-emitting diode 71. Further, the controller 74c is electrically connected to the PC body 3b, for transmitting the digital signals converted by the A-D converter 74b to the PC body 3b. Thus, the PC body 3b analyzes the digital signals received from the first optical information acquisition section 70 thereby obtaining absorbance values (intensity levels of transmitted lights) of the specimens stored in the cuvettes 152 with respect to the three lights emitted from the light-emitting diode 71, while analyzing the presence/absence, types and contents of the interference substances in the specimens. On the basis of the results of analysis, it is determined whether or not to measure the specimens with the second optical information acquisition section 80 and a method of analyzing detection signals from the second optical information acquisition section 80 and a method of displaying the results of analysis are controlled.

The second optical information acquisition section 80 has a function of warming the measurement samples prepared by adding the reagents to the specimens and detecting optical information from the measurement samples. This second optical information acquisition section 80 is constituted of the cuvette receiving section 81 and a detection section 82 (see FIG. 7) arranged under the cuvette receiving section 81. The cuvette receiving section 81 is provided with the 20 receiving holes 81a for receiving the cuvettes 152 and the reference light measurement hole 81b for measuring reference light without receiving any cuvette 152, as shown in FIG. 1. Further, the cuvette receiving section 81 has a built-in warming mechanism (not shown) for warming the cuvettes 152 received in the receiving holes 81a to a prescribed temperature.

Figure 7:
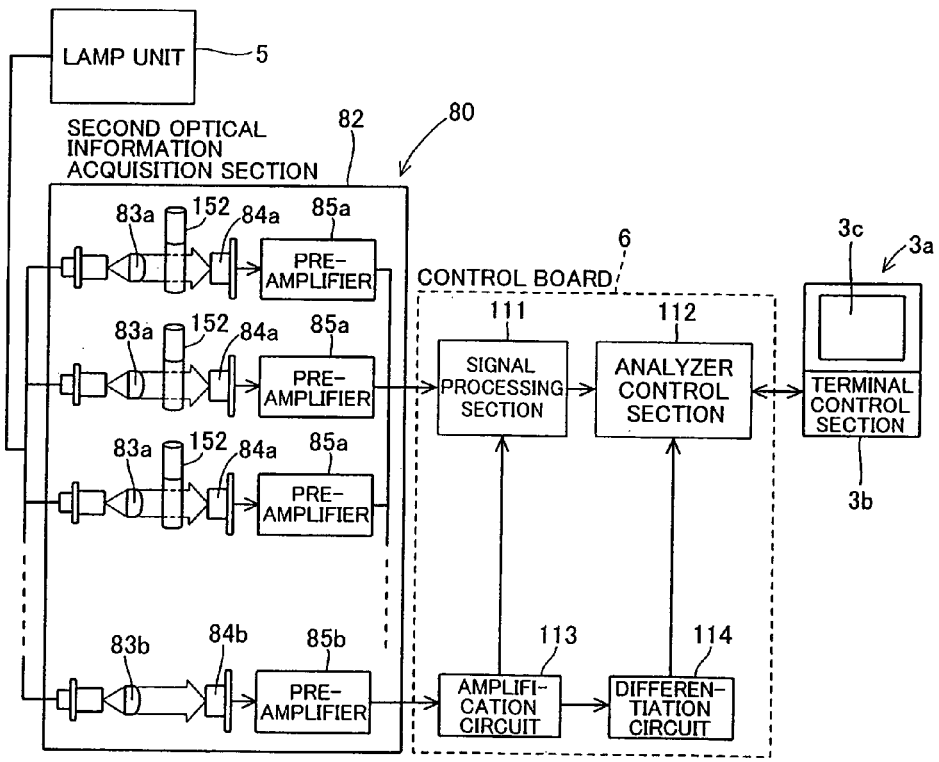
[FIG. 7] A block diagram for illustrating the structure of a second optical information acquisition section of the analyzer according to the first embodiment shown in FIG. 1.
Figure 8:
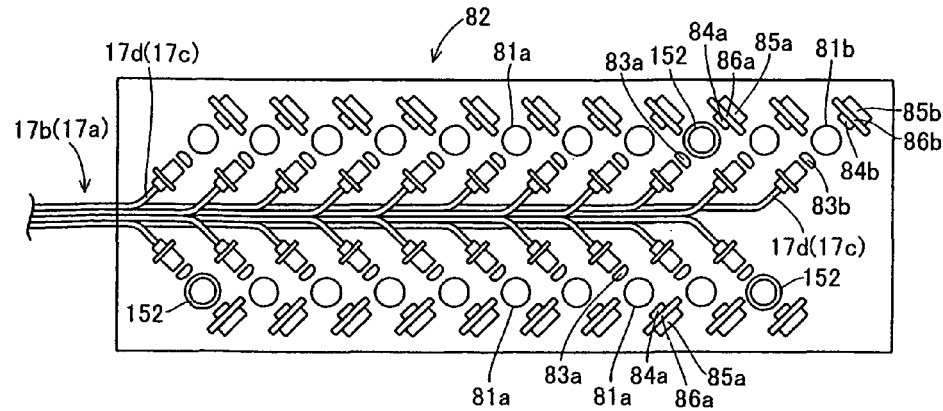
[FIG. 8] A schematic diagram showing the structure of a detection section of the second optical information acquisition section according to the first embodiment shown in FIG. 7.

The detection section 82 is so formed as to optically measure the measurement samples stored in the cuvettes 152 received in the receiving holes 81a. As shown in FIGS. 7 and 8, the detection section 82 is provided with collimator lenses 83a, photoelectric conversion elements 84a and preamplifiers 85a in correspondence to the receiving holes 81a receiving the cuvettes 152 respectively, and further provided with a reference light collimator lens 83b, a reference light photoelectric conversion element 84b and a reference light preamplifier 85b in correspondence to the reference light measurement hole 81b (see FIG. 1). The reference light collimator lens 83b, the reference light photoelectric conversion element 84b and the reference light preamplifier 85b are identical in structure to the collimator lenses 83a, the photoelectric conversion elements 84a and the preamplifiers 85a respectively.

As shown in FIG. 8, the collimator lenses 83a are set between ends of the optical fibers 17d (17c) guiding the lights received from the lamp unit 5 (see FIG. 1) and the corresponding receiving holes 81a. The collimator lenses 83a are provided for parallelizing the lights received from the optical fibers 17d (17c). The photoelectric conversion elements 84a are mounted on surfaces, closer to the receiving holes 81a, of substrates 86a opposite to the ends of the optical fibers 17d (17c) through the receiving holes 81a. The preamplifiers 85a are mounted on other surfaces of the substrates 86a opposite to the receiving holes 81a. The photoelectric conversion elements 84a have functions of detecting lights (hereinafter referred to as transmitted lights) transmitted through the measurement samples stored in the cuvettes 152 received in the receiving holes 81a upon photoirradiation and outputting electric signals (analog signals) corresponding to the detected transmitted lights. The preamplifiers 85a of the detection section 82 are provided for amplifying the electric signals (analog signals) received from the photoelectric conversion elements 84a.

The reference light collimator lens 83b, the reference light photoelectric conversion element 84b, the reference light preamplifier 85b and a reference light substrate 86b provided on the detection section 82 in correspondence to the reference light measuring hole 81b are identical in structure to the collimator lenses 83a, the photoelectric conversion elements 84a, the preamplifiers 85a and the substrates 86a provided on the detection section 82 in correspondence to the receiving holes 81a respectively. The reference light photoelectric conversion element 84b is so formed as to directly receive a light emitted from the corresponding optical fiber 17d (17c) and transmitted through the reference light collimator lens 83b as reference light. In other words, the reference light photoelectric conversion element 84b is so formed as to detect the reference light applied without through the cuvettes 152 storing the measurement samples and to output an electric signal (analog signal) corresponding to the detected reference light.

Figure 9:
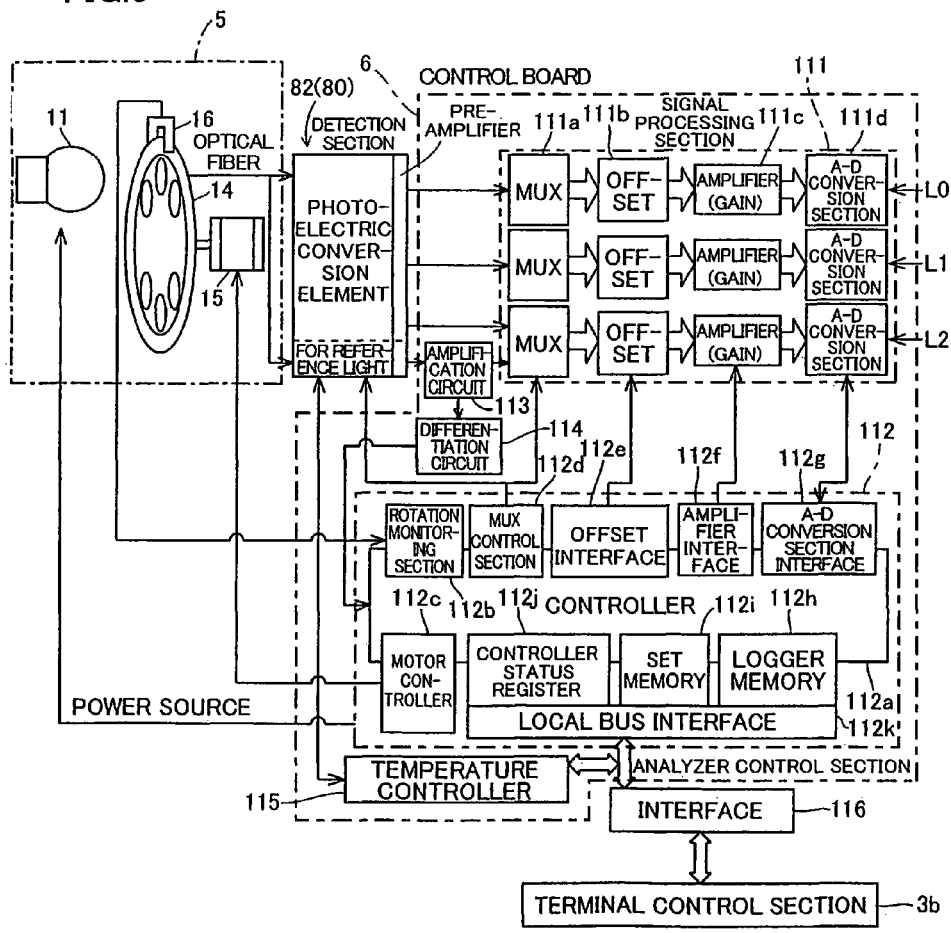
[FIG. 9] A block diagram for illustrating the components of the second optical information acquisition section and a control board of the analyzer according to the first embodiment of the present invention.

The control board 6 is arranged under the second optical information acquisition section 80. This control board 6 has a function of controlling operations of the analyzer 3 and the lamp unit 5 while processing and storing the optical information (electric signals) received from the second optical information acquisition section 80. As shown in FIGS. 7 and 9, the control board 6 is provided with the signal processing section 111, the control section 112, an amplification circuit 113, a differentiation circuit 114 and a temperature controller 115. The signal processing section 111 is provided for processing the signals output from the photoelectric conversion elements 84a detecting the transmitted lights when the lamp unit 5 irradiates the measurement samples with the lights. As shown in FIG. 9, this signal processing section II has three multiplexers (MUX) 111a, three offset circuits 111b, three amplifiers 111c and three A-D conversion sections 111d. The first multiplexer 111a, the first offset circuit 111b, the first amplifier 111c and the first A-D conversion section 111d constitute a signal processing line L0. In addition to this signal processing line L0, the signal processing section 111 is also provided with signal processing lines L1 and L2 similar in structure to the signal processing line L0. In other words, the signal processing section 1 is provided with the three signal processing lines L0 to L2 for processing the plurality of analog signals received from the detection section 82.

Figure 10:
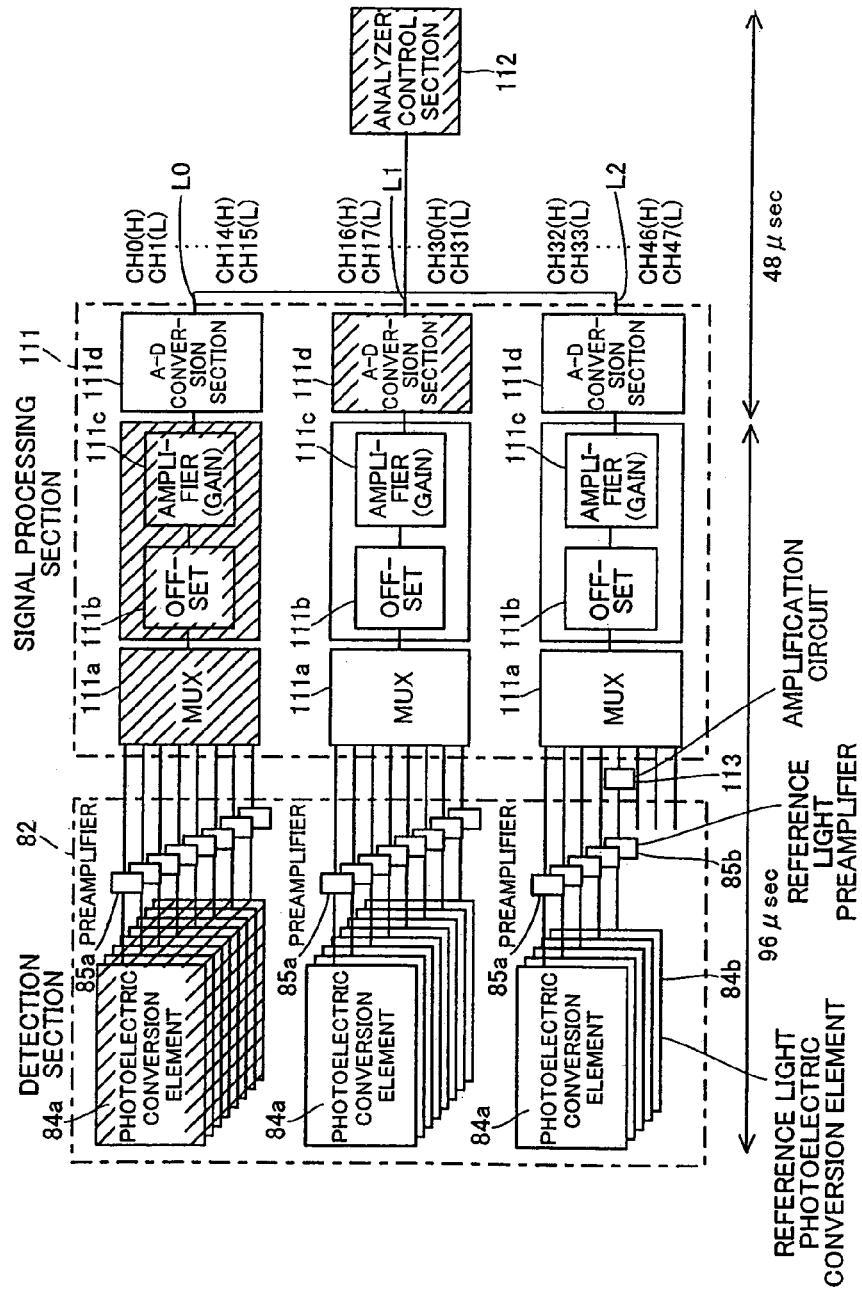
[FIG. 10] A block diagram for illustrating the structures of the detection section and a signal processing section of the analyzer according to the first embodiment of the present invention.

As shown in FIG. 10, the multiplexers 111a are connected to the plurality of preamplifiers 85a (reference light preamplifier 85b). These multiplexers 111a are so formed as to select the plurality of analog signals received from the plurality of photoelectric conversion elements 84a (reference light photoelectric conversion element 84b) through the preamplifiers 85a (reference light preamplifier 85b) one by one and to successively output the same to the offset circuits 111b. The offset circuits 111b have functions of correcting the signals received from the multiplexers 111a. More specifically, the offset circuits 111b are supplied with offset values corresponding to the receiving holes 81a or the reference light measurement hole 81b employed for measurement respectively from the control section 112 (see FIG. 9). The offset circuits 111b subtract these offset values from the signals corresponding to the transmitted lights received from the multiplexers 111a, thereby correcting the signals corresponding to the transmitted lights received from the multiplexers 111a.

The amplifiers 111c have functions of amplifying the analog signals received from the offset circuits 111b. The control section 112 controls the gains (amplification factors) of these amplifiers 111c, to be switchable between low gains and high gains higher than the low gains. Signals of the low gains (amplification factors) and the high gains (amplification factors) amplified by the amplifiers 111c are input in the A-D conversion sections 111d at different timing. The A-D conversion sections 111d, connected to the amplifiers 111c respectively, are provided for converting processed analog signals amplified to the signals (analog signals) of the low and high gains by the amplifiers 111c to digital signals (data).

According to the first embodiment, the A-D conversion sections 111d output 48 data (16 data per A-D conversion section) corresponding to channels CH0 to CH47 respectively, as shown in FIG. 10. Among these channels CH0 to CH47, the data of 42 channels CH0 to CH41 correspond to data based on the electric signals obtained from the photoelectric conversion elements 84a or the reference light photoelectric conversion element 84b respectively. In other words, the amplifiers 111c of the signal processing section 111 amplify 20 data obtained from 20 photoelectric conversion elements 84a to 40 data with the low and high gains (amplification factors). The amplifier 111c of the signal processing section 111 (see FIG. 9) amplifies single data obtained from the reference light photoelectric conversion element 84b to two data with the low and high gains (amplification factors). The data of the channels CH0 to CH41 correspond to 42 data obtained by totalizing the aforementioned 40 data and the two data corresponding to the reference light. The remaining six channels CH42 to CH47 among the channels CH0 to CH47 are preliminary channels not used in the first embodiment, and data of these channels CH42 to CH47 do not correspond to the electric signals from the photoelectric conversion elements 84a or the reference light photoelectric conversion element 84b.

The control section 112 has functions of controlling the operations of the analyzer 3 and acquiring and storing the digital signals (data) received from the A-D conversion sections 111d. As shown in FIG. 9, this control section 112 includes a controller 112a, the filter rotation monitoring section 112b, a motor controller 112c, a multiplexer control section 112d, an offset interface 112e, an amplifier interface 112f, an A-D conversion section interface 112g, a logger memory 112h, a set memory 112i, a controller status register 112j and a local bus interface 112k.

The controller 112a has a function of unifying various control operations with the control section 112. The filter rotation monitoring section 112b is provided for monitoring whether or not the filter section 14 of the lamp unit 5 normally rotates. This filter rotation monitoring section 112b is so formed as to receive the detection signals from the sensor 16 detecting passage of the origin slit 14k (see FIG. 5) or the normal slits 14l following rotation of the filter section 14. The filter rotation monitoring section 112b monitors whether or not the filter section 14 normally rotates by monitoring the time intervals of the detection signals for the origin slit 14k (see FIG. 5) and the normal slits 14l (see FIG. 5) output from the sensor 16 and the frequency of the detection signals for the normal slits 14l output between pairs of detection signals for the origin slit 14k output from the sensor 16. The motor controller 112c has a function of controlling the rotational frequency of the motor 15 rotating the filter section 14. The multiplexer control section 112d has a function of controlling operations of the multiplexers 111a. More specifically, the multiplexer control section 112d controls the operations of the plurality of multiplexers 111a to select the analog signals at different times respectively.

The controller 112a is so formed as to control operations of the offset circuits 111b, the amplifiers 111c and the A-D conversion sections 111d of the signal processing section 111 through the offset interface 112e, the amplifier interface 112f and the A-D conversion section interface 112g respectively, as shown in FIG. 9. More specifically, the controller 112a supplies prescribed offset values to the offset circuits 111b through the offset interface 112e, while controlling the offset circuits 111b to perform correction processing by subtracting the offset values from the signals received from the multiplexers 111a. The controller 112a controls the amplifiers 111c between the low and high gains through the amplifier interface 112f, while controlling the amplifiers 111c to amplify the signals received from the offset circuits 111b. Further, the controller 112a controls the A-D conversion sections 111d to convert the signals (analog signals) received from the amplifiers 111c to digital signals through the A-D conversion section interface 112g. The logger memory 112h receives and stores the digital signals (data) acquired by the A-D conversion sections 111d through the A-D conversion section interface 112g and the controller 112a. At this time, the controller 112a controls operations of the A-D conversion sections 111d through the A-D conversion section interface 112g, not to overlap the periods for outputting the digital signals respectively with each other.

The controller 112a also has a function of switching that executing processing among the multiplexers 111a, the offset circuits 111b, the amplifiers 111c and the A-D conversion sections 111d of the signal lines L0 to L2 and the logger memory 112h, so that the A-D conversion section 111d of another signal processing line performs conversion processing and the logger memory 112h of the control section 112 stores data while the multiplexer 111a, the offset circuit 111b and the amplifier 111c of a prescribed signal processing line L0, L1 or L2 process the corresponding analog signals. This point is described later in more detail with reference to an analytic operation.

Figure 11:
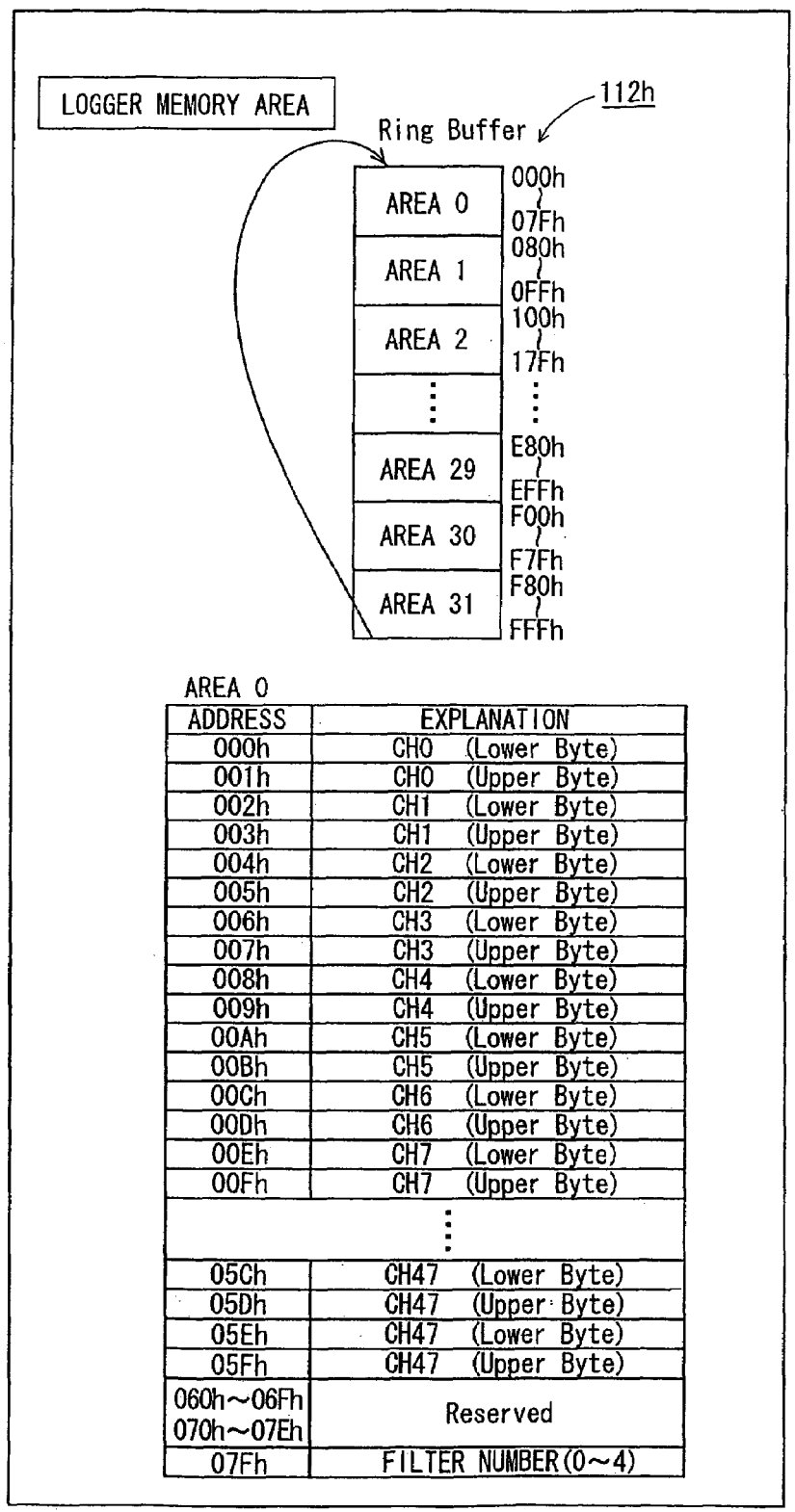
[FIG. 11] A diagram for illustrating the structure of a logger memory of the control board of the analyzer according to the first embodiment of the present invention.

The logger memory 112h is provided for storing the digital signals (data) corresponding to the analog signals output from the photoelectric conversion elements 84a to be identifiable with addresses of the logger memory 112h. As shown in FIG. 11, the logger memory 112h is constituted of 32 areas 0 to 31 in units of 128 bytes. The areas 0 to 31 store data corresponding to the lights transmitted through the five optical filters 14b to 14f (see FIG. 5) and data corresponding to the blocked hole 14j respectively. In other words, every rotation of the filter section 14 results in data corresponding to the lights transmitted through the five optical filters 14b to 14f having different light transmission characteristics. The logger memory 112h (see FIG. 11) stores these data successively from the area 0. The logger memory 112h stores "0" in every sixth area as the data corresponding to the hole 14j. Thus, the logger memory 112h uses six areas every rotation (about 100 msec.) of the filter section 14. After using the areas 0 to 31 up to the final area 31, the logger memory 112h returns to the area 0 for overwriting data.

Each of the areas 0 to 31 of the logger memory 112h has 128 addresses. For example, the area 0 has 128 addresses 000h to 00Fh, 010h to 01Fh, 020h to 02Fh, 030h to 03Fh, 040h to 04Fh, 050h to 05Fh, 060h to 06Fh and 070h to 07Fh. Further, the area 0 is so formed as to store the data of the aforementioned channels CH0 to CH47 (see FIG. 10) in the 96 addresses 000h to 05Fh. Each of the data of the channels CH0 to CH47 is stored in two addresses. According to the first embodiment, the channels CH42 to 47 output no data as hereinabove described, so that addresses corresponding to these channels store no data.

The addresses 060h to 06Fh and 070h to 07Eh in the area 0 of the logger memory 112h shown in FIG. 11 are preliminary addresses storing no data in the first embodiment. The area 0 stores filter numbers (0 to 4) in the final address 07Fh. These filter numbers (0 to 4) are employed for identifying the five optical filters 14b to 14f (see FIG. 5) respectively. The optical filters can be identified by detecting the timing of passage of the origin slit 14k. The filter numbers (0 to 4) corresponding to the five optical filters 14b to 14f are stored in the address 07Fh, thereby identifying the optical filter (one of 14b to 14f) through which the light corresponding to the data stored in the area 0 has been transmitted.

The set memory 112i shown in FIG. 9 is provided for storing set values such as the offset values supplied to the offset circuits 111b and the gains (amplification factors) supplied to the amplifiers 111c. The controller status register 112j is provided for temporarily storing information such as whether or not the filter section 14 normally rotates, presence/absence of errors in analog-to-digital conversion by the A-D conversion sections 111d, the status of data acquisition by the PC body 3b from the logger memory 112h and presence/absence of an instruction for starting measurement from the PC body 3b. The control section 112 has a function of transmitting the data (optical information) of the measurement samples stored in the logger memory 112h to the PC body 3b through the local bus interface 112k and an interface 116.

Figure 12:
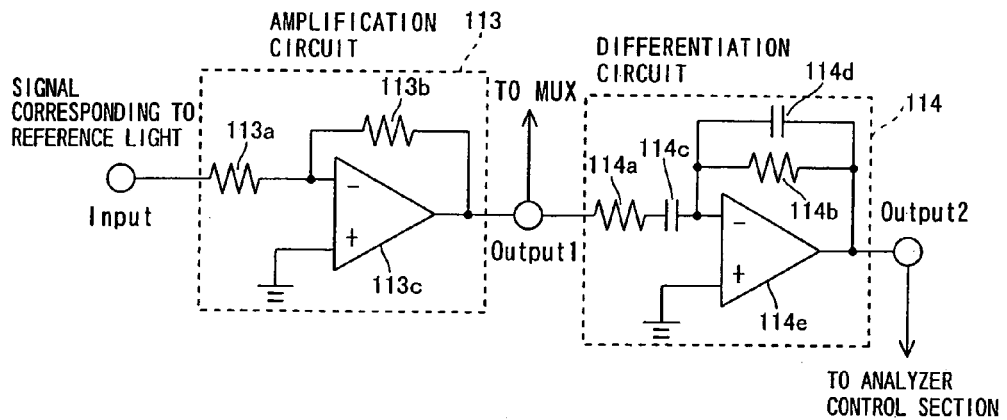
[FIG. 12] A circuit diagram showing the circuit structures of an amplification circuit and a differentiation circuit of the control board of the analyzer according to the first embodiment of the present invention.

The amplification circuit 113 of the control board 6 shown in FIG. 9 has a function of receiving the signal output from the reference light photoelectric conversion element 84b (see FIG. 10) through the reference light preamplifier 85b and amplifying the received signal. As shown in FIG. 12, this amplification circuit 113 is constituted of two resistors 113a and 113b and an operational amplifier 113c. A first end of the resistor 113a receives the signal corresponding to the reference light from the reference light preamplifier 85b, while a second end thereof is connected to an inverted input terminal of the operational amplifier 113c. The resistor 113b is connected between an output terminal and the inverted input terminal of the operational amplifier 113c. A non-inverted input terminal of the operational amplifier 113c is grounded. The multiplexers 111a of the signal processing section 111 (see FIG. 9) and the differentiation circuit 114 receive an output of the operational amplifier 113c.

The differentiation circuit 114 of the control board 6 has a function of generating a differential signal of the signal (hereinafter referred to as a reference signal) corresponding to the reference light received from the amplification circuit 113. As shown in FIG. 12, this differentiation circuit 114 is constituted of two resistors 114a and 114b, two capacitors 114c and 114d and an operational amplifier 114e. A first end of the resistor 114a receives the reference signal from the amplification circuit 113, while a second end thereof is connected to a first electrode of the capacitor 114c. A second electrode of the capacitor 114c is connected to an inverted input terminal of the operational amplifier 114e. Both of the resistor 114b and the capacitor 114d are connected between an output terminal and the inverted input terminal of the operational amplifier 114e. A non-inverted input terminal of the operational amplifier 114e is grounded. The controller 112a of the control section 112 (see FIG. 9) receives an output of the operational amplifier 114e through a comparator (not shown).

The temperature controller 115 of the control board 6 shown in FIG. 9 has a function of controlling the temperature of the cuvette receiving section 81 (see FIG. 1) receiving the cuvettes 152 by controlling another warming mechanism (not shown) stored in the second optical information acquisition section 80. As shown in FIG. 9, the temperature controller 115 is so formed as to control warming with the warming mechanism (not shown) of the second optical information acquisition section 80 in response to a set temperature (about 37° C.) received from the PC body 3b through the interface 116.

The outline of control of the analyzer 3 with the PC body 3b is now described with reference to FIGS. 2, 3 and 13. The analyzer 3 and the extension analyzer 4 are identical in control to each other, and hence the control of the analyzer 3 is described in the following.

The analytic system 1 starts the information processing terminal 3a, the body of the analyzer 3 and the extension analyzer 4 by supplying power thereto.

Figure 13:
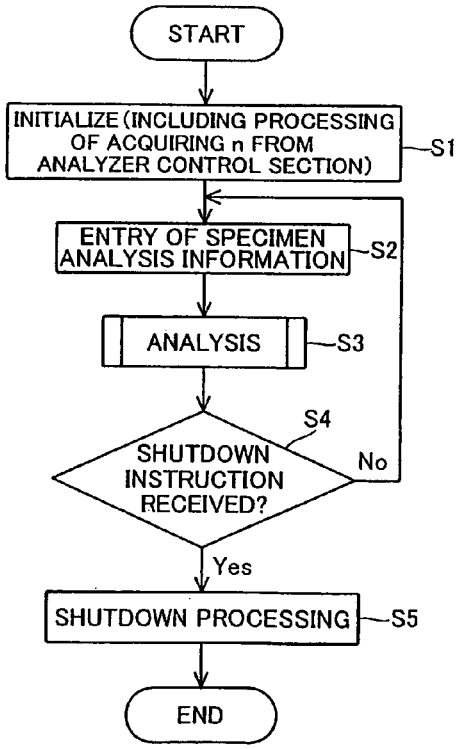
[FIG. 13] A flow chart showing the outline of a control method by a PC body according to the first embodiment of the present invention.

Upon this power supply, the PC body 3b performs initialization at a step S1 shown in FIG. 13. In this initialization, the PC body 3b initializes software stored therein and performs processing of acquiring n clocks described later from the control section 112 of the analyzer 3. Upon power supply to the body of the analyzer 3, the halogen lamp 11 of the lamp unit 5 (see FIG. 3) applies light while the filter section 14 starts rotating at a constant rotational speed of 10 revolutions/sec. in the initialization at the step S1. The halogen lamp 11 continuously applies light and the filter section 14 continuously rotates until the body of the analyzer 3 is turned off. At a step S2, entry of specimen analysis information by the user is accepted. In other words, the user inputs information in columns of specimen numbers and measurement items of a specimen analysis list output on the display section 3c of the information processing terminal 3a (see FIG. 2) through the keyboard 3d of the information processing terminal 3a. The PC body 3b preserves the specimen analysis information.

At a step S3, the PC body 3b instructs analysis, so that the analyzer 3 performs the analysis. At a step S4, the PC body 3b determines whether or not a shutdown instruction for the analytic system 1 has been received. When determining that no shutdown instruction for the analytic system 1 has been received at the step S4, the PC body 3b returns to the step S2 for accepting entry of another specimen analysis information by the user. When determining that a shutdown instruction for the analytic system 1 has been received at the step S4, on the other hand, the PC body 3b performs shutdown processing at a step S5. According to this shutdown processing, the analytic system 1 automatically enters an OFF-state, thereby completing the operation thereof.

A method of calculating the n clocks with the control section 112 is now described with reference to FIGS. 3, 7 to 9, 14 and 15.

Figure 15:
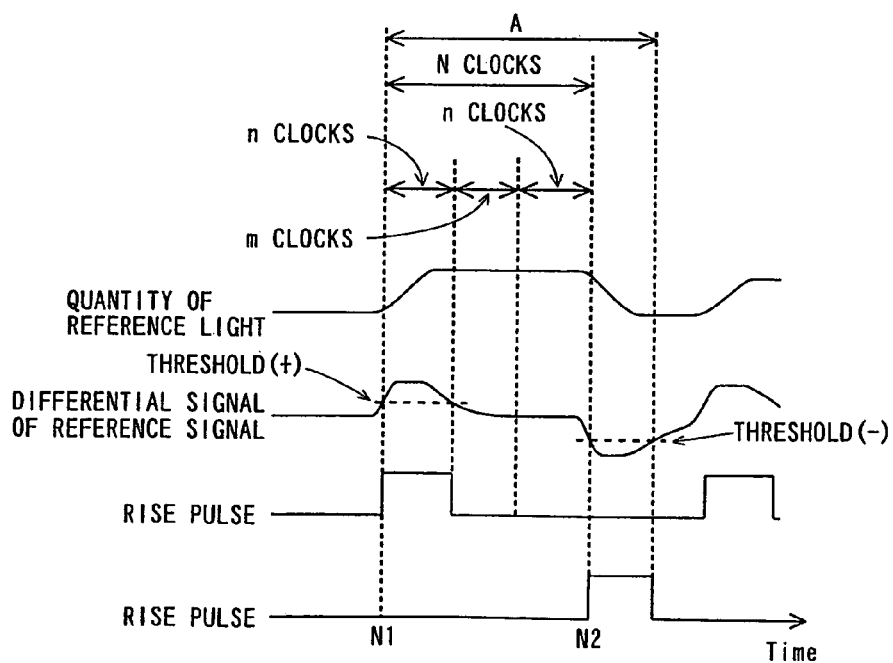
[FIG. 15] A waveform diagram showing changes in the quantity of reference light and a differential signal of a reference signal employed in the method of calculating n clocks shown in FIG. 14.

As shown in FIG. 15, the quantity of the reference light incident upon the reference light photoelectric conversion element 84b (see FIG. 8) from the lamp unit 5 changes along a waveform shown as "QUANTITY OF REFERENCE LIGHT" during the constant speed rotation of the filter section 14 (see FIG. 3). Referring to FIG. 15, symbol A denotes a period when any one of the optical filters 14b to 14f of the rotating filter section 14 is arranged on the path of the corresponding light from the halogen lamp 11 in the lamp unit 5 (see FIG. 3). When the aforementioned one of the optical filters 14b to 14f approaches the path of the corresponding light from the halogen lamp 11 in this period A, the quantity of the reference light gradually increases. Thereafter the path of the corresponding light from the halogen lamp 11 completely falls into the aforementioned one of the optical filters 14b to 14f, so that the quantity of the reference light is constant. When the aforementioned one of the optical filters 14b to 14f thereafter starts deviating from the path of the corresponding light from the halogen lamp 11, the quantity of the reference light starts to gradually decrease. When the aforementioned one of the optical filters 14b to 14f completely deviates from the path of the corresponding light from the halogen lamp 11, the quantity of the reference light reaches zero.

As shown in FIG. 7, the reference light photoelectric conversion element 84b converts the reference light to an electric signal, so that the reference light preamplifier 85b and the amplification circuit 113 amplify the converted electric signal. The amplification circuit 113 outputs a signal (hereinafter referred to as a reference signal) corresponding to the reference light, so that the differentiation circuit 114 receives this reference signal. The differentiation circuit 114 generates a differential signal of the reference signal having a waveform shown as "DIFFERENTIAL SIGNAL OF REFERENCE SIGNAL" in FIG. 15. The control section 112 receives this differential signal of the reference signal from the differentiation circuit 114 (see FIG. 9) through the comparator (not shown).

Figure 14:
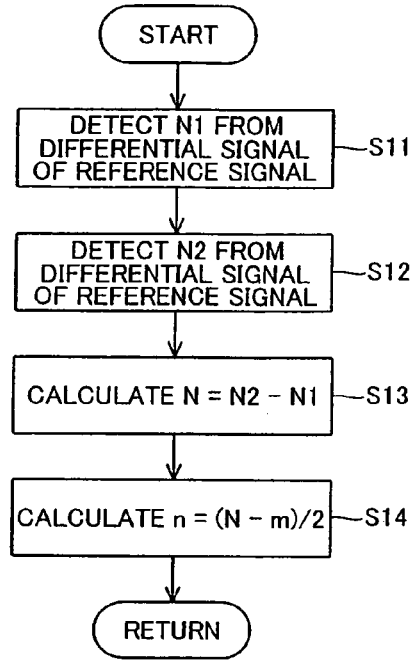
[FIG. 14] A flow chart showing a method of calculating n clocks acquired by the PC body with a control section in initialization shown at a step S1 in FIG. 13.

At a step S11 shown in FIG. 14, the control section 112 detects a clock number N1 at a point of time when the differential signal of the reference signal reaches a prescribed negative threshold (+). More specifically, the differential signal of the reference signal rises following increase of the quantity of the reference light, as shown in FIG. 15. In response to the differential signal reaching the prescribed positive threshold (+), the comparator (not shown) receiving the differential signal from the differentiation circuit 114 (see FIG. 9) outputs a pulse signal rising to a high level. The controller 112a of the control section 112 receives this pulse signal, and detects the clock number N1 at the point of time when the pulse signal has risen to the high level. Thus, the controller 112a of the control section 112 detects the clock number N1 at the point of time when the differential signal of the reference signal reaches the prescribed positive threshold (+).

Thereafter the quantity of the reference light further increases and reaches a prescribed constant value, as shown in FIG. 15. Thereafter the quantity of the reference light gradually decreases. Following this, the differential signal of the reference signal gradually falls. At a step S12 shown in FIG. 14, the control section 112 detects a clock number (N2) at a point of time when the differential signal of the reference signal reaches a prescribed negative threshold (−). More specifically, the comparator (not shown) receiving the differential signal from the differentiation circuit 114 (see FIG. 9) outputs a pulse signal rising to a high level in response to the differential signal of the reference signal gradually falling and reaching the prescribed negative threshold (−). The controller 112a of the control section 112 receives this pulse signal, and detects the clock number N2 at the time when the pulse signal has risen to the high level. Thus, the controller 112a of the control section 112 detects the clock number N2 at the time when the differential signal of the reference signal reaches the prescribed negative threshold (−).

At a step S13 in FIG. 14, the control section 112 calculates the number of clocks (N clocks) counted between the clock numbers N1 and N2 according to a formula N=N2−N1. At a step S14, the control section 112 calculates the clock number (n clocks) for deciding the timing for starting acquiring the signals corresponding to the lights transmitted through the measurement samples according to a formula n=(N−m)/2, where symbol m represents the number of clocks previously set as a proper period necessary for the control section 112 for acquiring the signals corresponding to the lights transmitted through the measurement samples. According to the first embodiment, the control section 112 calculates the timing for starting acquiring the signals corresponding to the transmitted lights with the reference light not influenced by the measurement samples etc. As understood from FIG. 15, signals in a period where the quantities of the lights applied from the lamp unit 5 are stable can be acquired by acquiring the signals corresponding to the lights transmitted through the measurement samples from the detection section 82 for the period of m clocks with the multiplexers 111a after n clocks calculated in the aforementioned manner from the clock N1.

The aforementioned processing at the step S3 in FIG. 13 is now described in detail with reference to FIGS. 1, 2, 5 to 11, 13 and 16 to 18. At a step S21 shown in FIG. 16, the PC body 3b instructs primary measurement. Thus, the aforementioned first optical information acquisition section 70 measures interference substances in the specimens. The PC body 3b receives the optical information acquired by the first optical information acquisition section 70 through the controller 74c.

At a step S22, the PC body 3b analyzes the received optical information, and determines whether or not the primarily measured specimens are to be subjected to secondary measurement with the second optical information acquisition section 80 on the basis of the results of the analysis. When determining that the specimens are not to be subjected to secondary measurement, the PC body 3b makes the display section 3c display a message indicating that it is difficult to perform reliable analysis due to remarkable influence by interference substances contained in these specimens (step S28). When determining that the specimens are to be subjected to secondary measurement at the step S22, on the other hand, the PC body 3b instructs suction of the specimens at a step S23. Thus, the specimen injection arm 40 sucks the specimens from the cuvettes 152 held on the rotary transport section 30.

At a step S24, the PC body 3b instructs preparation of measurement samples. Thus, the specimen injection arm 40 injects the sucked specimens into the plurality of cuvettes 152 while the reagent injection arms 50 add the reagents for starting blood coagulation contained in the reagent vessels (not shown) to the specimens stored in the plurality of cuvettes 152 in the analyzer 3. Thus, the measurement samples are prepared. Then, the cuvette transfer section 60 moves the cuvettes 152 storing the measurement samples toward the receiving holes 81a of the cuvette receiving section 81 of the second optical information acquisition section 80.

At a step S25, the PC body 3b instructs secondary measurement. Thus, the analyzer 3 starts secondary measurement of the measurement samples. This secondary measurement is hereinafter described in detail.

As hereinabove described, the lamp unit 5 intermittently successively irradiates the cuvettes 152 moved toward the receiving holes 81a with the five types of lights having different wavelength characteristics (340 nm, 405 nm, 575 nm, 660 nm and 800 nm) respectively. The lights transmitted through the cuvettes 152 are converted to digital data through the photoelectric conversion elements 84a, the preamplifiers 85a, the multiplexers 111a, the offset circuits 111b, the amplifiers 111c and the A-D conversion sections 111d and stored in the logger memory 112h.

Operations of the signal processing section 11 are now described with reference to FIG. 10.

The three signal processing lines L0 to L2 constituted of the multiplexers 111a, the offset circuits 111b, the amplifiers 111c and the A-D conversion sections 111d partially parallelly process the electric signals with the multiplexers 111a, the offset circuits 111b, the amplifiers 111c and the A-D conversion sections 111d. In other words, as shown in FIG. 10, the signal processing line L0 processes the corresponding electric signals with the multiplexer 111a, the offset circuit 111b and the amplifier 111c, the signal processing line L1 converts the corresponding electric signals with the A-D conversion section 111d and the logger memory 112h (see FIG. 9) of the control section 112 stores data in parallel with each other. Similarly, the signal processing line L1 processes the corresponding electric signals with the multiplexer 111a, the offset circuit 111b and the amplifier 111c, the signal processing line L2 converts the corresponding electric signals with the A-D conversion section 111d and the logger memory 112h (see FIG. 9) of the control section 112 stores data in parallel with each other. Further, the signal processing line L2 processes the corresponding electric signals with the multiplexer 111a, the offset circuit 111b and the amplifier 111c, the signal processing line L0 converts the corresponding electric signals with the A-D conversion section 111d and the logger memory 112h (see FIG. 9) of the control section 112 stores data in parallel with each other.

Figures 17, 18:
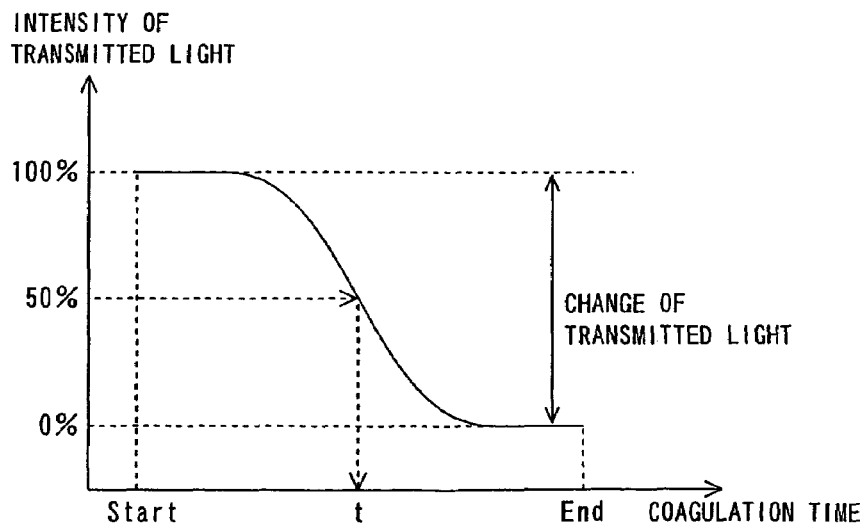
[FIG. 17] A diagram showing a signal processing method in the signal processing section of the analyzer according to the first embodiment of the present invention.
[FIG. 18] A graph showing a coagulation curve created by the analytic system according to the first embodiment of the present invention.

The signal processing section 111 partially parallelly processes the electric signals in units of 48 μsec. by successively using the three signal processing lines L0 to L2, as shown in FIG. 17. More specifically, the signal processing line L0 performs switching to the channel CH0 with the multiplexer 111a, correction with the offset circuit 111b and amplification with the amplifier 111c at a step 0 shown in FIG. 17. At this step 0, the signal processing lines L1 and L2 are in states waiting for stabilization of the corresponding electric signals (signal wait states), to process no electric signals. At a step S1 in FIG. 17, the signal processing line L1 performs switching to the channel CH6 with the multiplexer 111a, correction with the offset circuit 111b and amplification with the amplifier 111c. At this step S1, the signal processing lines L0 and L1 are in states waiting for stabilization of the corresponding electric signals, to process no electric signals.

At a step S2 in FIG. 17, the signal processing line L0 performs A-D conversion of the electric signal of the channel CH0 with the A-D conversion section 111d, the logger memory 112h stores data and the signal processing line L2 performs switching to the channel CH32 with the multiplexer 111a, correction with the offset circuit 111b and amplification with the amplifier 111c in parallel with each other. At the step S2, the signal processing line L1 is in a state waiting for stabilization of the corresponding electric signals, not to process the electric signals.

At a step S3 in FIG. 17, the signal processing line L0 performs switching to the channel CH1 with the multiplexer 111a, correction with the offset circuit 111b and amplification with the amplifier 111c, the signal processing line L1 performs A-D conversion of the electric signal of the channel CH16 with the A-D conversion section 111d and the logger memory 112h stores data in parallel with each other. At this step S3, the signal processing line L2 is in a state waiting for stabilization of the corresponding electric signals, not to process the electric signals.

At a step S4 in FIG. 17, the signal processing line L1 performs switching to the channel CH17 with the multiplexer 111a, correction with the offset circuit 111b and amplification with the amplifier 111c, the signal processing line L2 performs A-D conversion of the electric signal of the channel CH32 with the A-D conversion section 111d and the logger memory 112h stores data in parallel with each other. At this step S4, the signal processing line L0 is in a state waiting for stabilization of the corresponding electric signals, not to process the electric signals.

The signal processing lines L0 to L2 repetitively perform parallel processing similar to that through the aforementioned steps S2 to 4 up to a step S49 while switching the channels for signal processing. At a step S50, the signal processing line L2 performs switching to the channel CH32 with the multiplexer 111a, correction with the offset circuit 111b and amplification with the amplifier 111c. At the step S50, the signal processing lines L0 and L1 are in states waiting for stabilization of the corresponding electric signals, not to process the electric signals.

All output signals of the multiplexers 111a, the offset circuits 111b and the amplifiers 111c are unstable immediately after signal processing. According to the first embodiment, the aforementioned periods for waiting for stabilization of the electric signals are so provided as to prevent such unstable signals from application to analysis of analyzing objects.

The electric signals of all channels CH0 to CH47 through the 51 steps S0 to 50 are processed in the aforementioned manner. The electric signals through the 51 steps are processed in a period of 2.45 msec. (=48 μsec.×51 steps). Further, the electric signals through the 51 steps are processed once in a period of data acquisition processing of m clocks described later.

As hereinabove described, the logger memory 112h stores data in prescribed addresses, for specifying the optical filters and the channels transmitting the lights received from the halogen lamp 11. Thus, the logger memory 112h transmits the data stored therein to the PC body 3b at prescribed timing.

Figure 16:
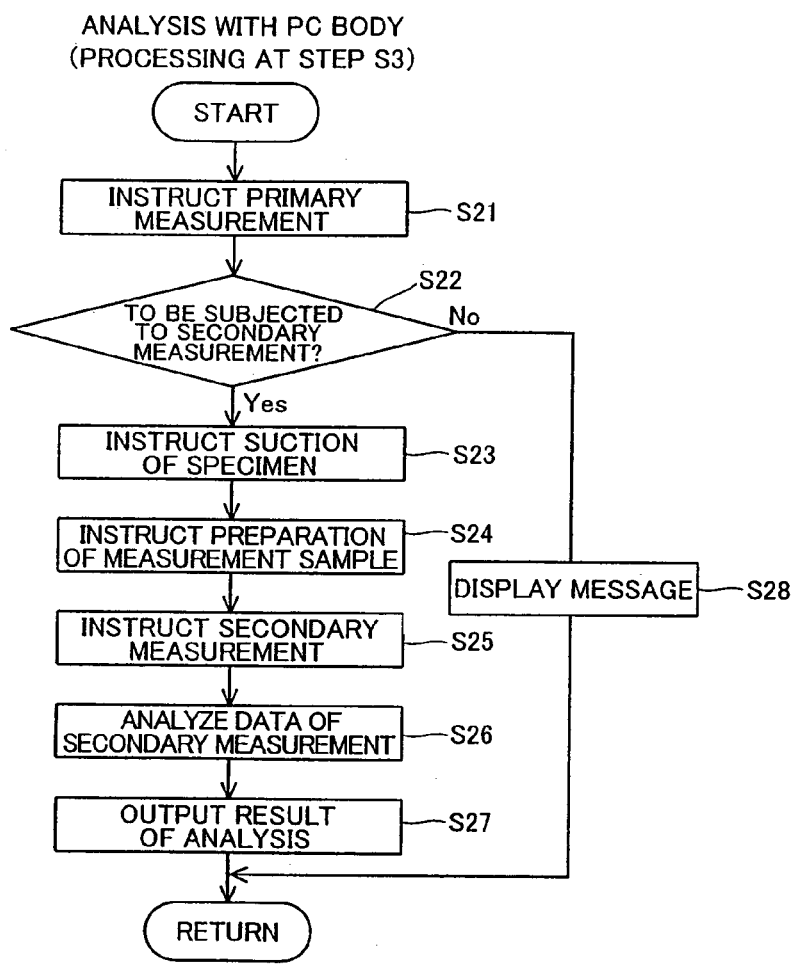
[FIG. 16] A flow chart showing the details (subroutine) of analysis with the PC body at a step S3 in FIG. 13.

At a step S26 in FIG. 16, the PC body 3b selects optical information (data) suitable for analysis from among 10 types of optical information (data) having different wavelength characteristics and different amplification rates received from the second optical information acquisition section 80, i.e., among data of the low and high gains corresponding to the five types of optical filters 14b to 14f respectively, on the basis of the results of analysis of the optical information (data) from the first optical information acquisition section 70 acquired at the step S22 and analyzes the optical information. At a step S27, the results of analysis of the measurement samples (coagulation curve and coagulation time shown in FIG. 18 in the first embodiment) is output to the display section 3c.

Data acquisition with the control section 112 according to the first embodiment is now described with reference to FIGS. 9, 13, 15, 17 and 19. The PC body 3b instructs analysis (step S3), in order to start this data acquisition.

Figure 19:
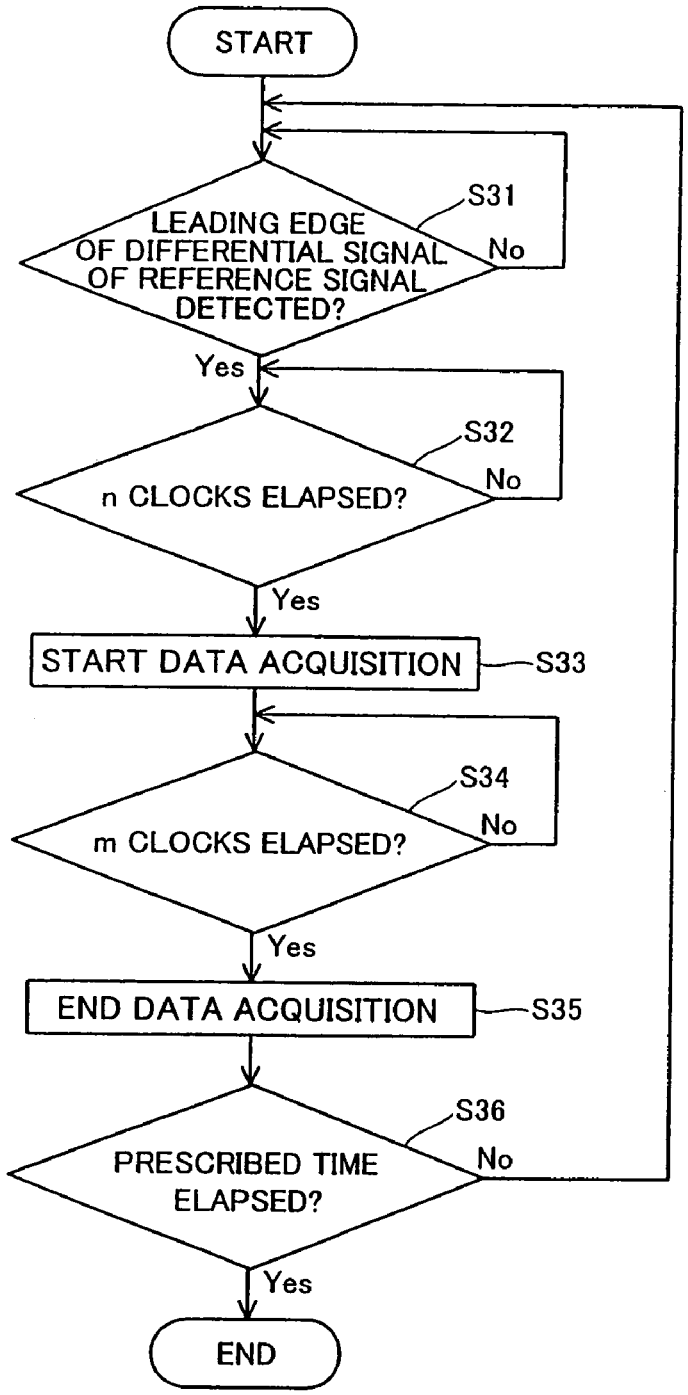
[FIG. 19] A flow chart for illustrating a method of data acquisition with the control section according to the first embodiment of the present invention.
Figure 20:
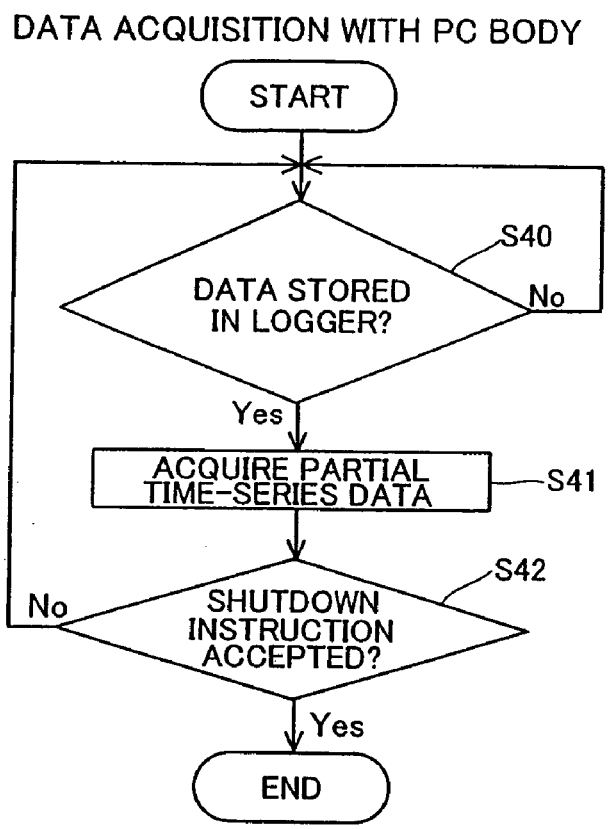
[FIG. 20] A flow chart for illustrating a method of data acquisition with the PC body according to the first embodiment of the present invention.

At a step S31 shown in FIG. 19, the control section 112 (FIG. 9) waits for detection of the leading edge of the differential signal of the reference signal corresponding to N1 in FIG. 15. When detecting the leading edge of the differential signal of the reference signal, the control section 112 waits for a lapse of n clocks calculated in the initialization from the leading edge of the differential signal of the reference signal at a step S32.

At a step S33, the control section 112 starts acquiring digital data output from the three A-D conversion sections 11d respectively. At a step S34, the control section 112 waits for a lapse of m clocks from the start of digital data acquisition. Upon the lapse of m clocks, the control section 112 ends the digital data acquisition at a step S35. At a step S36, the control section 112 determines whether or not a prescribed time has elapsed from the time receiving the instruction for analysis from the PC body 3. The data acquisition is ended if the prescribed time has elapsed, while returning to the step S31 if the prescribed time has not yet elapsed.

Data acquisition with the PC body 3b according to the first embodiment is now described with reference to FIGS. 1, 9, 11, 18 and 20. This processing is started upon power supply to the information processing terminal 3a.

At a step S40, the PC body 3b monitors whether or not the logger 112h has newly stored data, and waits until the logger 112h stores data for 100 msec. (corresponding to single rotation of the filter section 14). More specifically, the PC body 3b waits for transmission of a notice from the control section 112 indicating that the logger 112h has stored data for 100 msec. At a step S41, the PC body 3b acquires the data (partial time-series data) for 100 msec. from the logger memory 112h through the interface 116 and the local bus interface 112k. In other words, the PC body 3b acquires data for 100 msec. corresponding to single rotation of the filter section 14 stored in the areas 0 to 5 of the logger memory 112h as shown in FIG. 11.

At a step S42, the PC body 3b determines whether or not the information processing terminal 3a has accepted a shutdown instruction. When the information processing terminal 3a has accepted no shutdown instruction, the PC body 3b returns to the step S40. When the information processing terminal 3a has accepted the shutdown instruction, on the other hand, the PC body 3b ends the data acquisition. When carrying out the step S41 for the second time, the PC body 3b acquires data from the six areas 6 to 11 of the logger memory 112h subsequent to the areas 0 to 5, from which the data have been acquired at the first time. Thus, the PC body 3b successively acquires data from the logger memory 112h every six areas.

The PC body 3b creates prescribed time-series data by combining partial time-series data subsequent to the time when the cuvettes 152 (see FIG. 1) storing the measurement samples have been received in the receiving holes 81a of the second optical information acquisition section 80 among those acquired from the logger memory 112h at the step S41 in a time-series manner. Then, the PC body 3b creates the coagulation curve shown in FIG. 18 on the basis of the created time-series data, and obtains the coagulation times of the measurement samples from the created coagulation curve. More specifically, the PC body 3b obtains a time t when the intensity of the transmitted lights reaches 50%, i.e., the intermediate level between 100% and 0% in a graph of the coagulation curve shown in FIG. 18, and calculates elapsed times from this time t as the coagulation times. The display section 3c displays the coagulation times at the step S27 (see FIG. 16), as described above.

Monitoring on the rotation of the filter section 14 is hereinafter described.

The control section 112 parallelly and continuously executes the following three monitoring operations during the rotation of the filter section. When causing an error in at least one of the three monitoring operations, rotation of the filter section 14 is stopped. The methods of the aforementioned three monitoring operations on the rotation of the filter section 14 are hereinafter described in detail.

A method of monitoring the time interval for detecting the origin slit 14k is described with reference to FIGS. 2, 3, 9, 21 and 22. According to the first embodiment, the filter section 14 of the lamp unit (see FIG. 3) uninterruptedly rotates at a constant speed while a power source of the analyzer 3 (see FIG. 2) is in an ON-state. At this time, the filter rotation monitoring section 112b of the control section 112 (see FIG. 9) receives signals from the sensor 16 detecting the slits of the rotating filter section 14. When detecting the slits, the sensor 16 outputs a signal rising to ON-states as shown in a waveform diagram of FIG. 22. At a step S51 shown in FIG. 21, the filter rotation monitoring section 112b determines whether or not the sensor 16 has detected any slit on the basis of the signal received from the sensor 16. When determining that the sensor 16 has detected no slit at the step S51, the filter rotation monitoring section 112b repetitively determines whether or not the sensor 16 has detected passage of any slit at the step S51 again.

Figure 21:
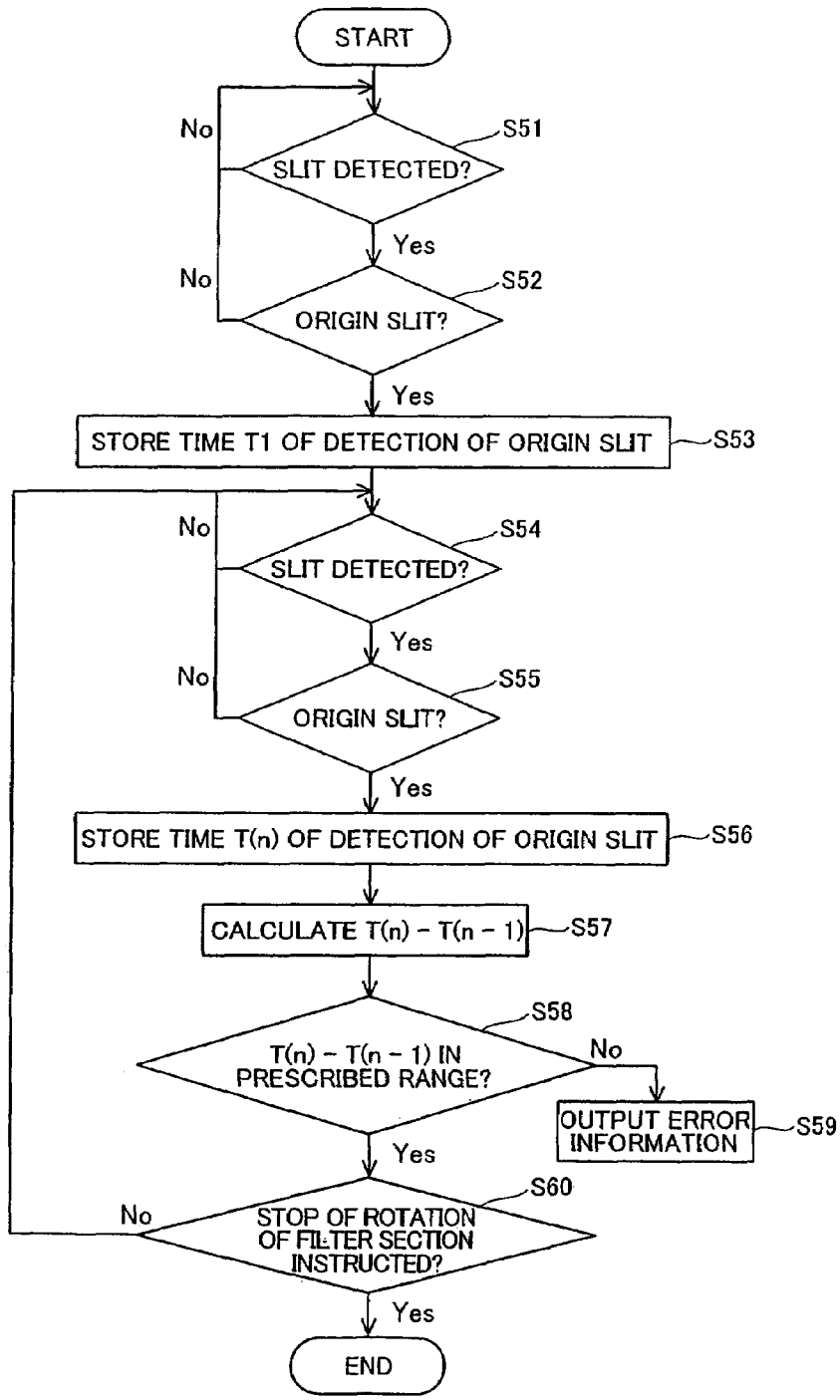
[FIG. 21] A flow chart showing processing of monitoring a time interval for detecting an origin slit in processing of monitoring rotation of the filter section with the control section according to the first embodiment of the present invention.
Figure 22:
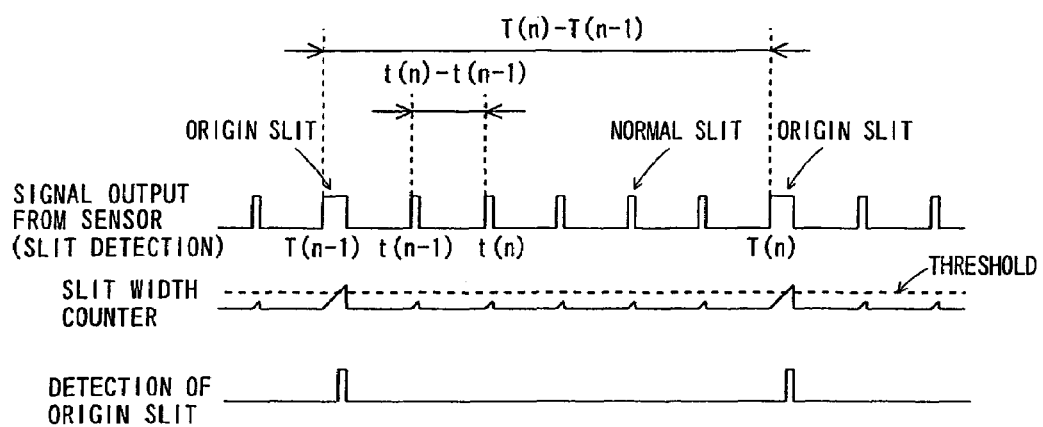
[FIG. 22] A waveform diagram showing the waveforms of a signal output from a sensor detecting slits of the rotating filter section and an integral signal generated on the basis of the signal output from the sensor.

When determining that the sensor 16 has detected any slit at the step S51 shown in FIG. 21, on the other hand, the filter rotation monitoring section 112b of the control section 112 determines whether or not this slit is the origin slit 14k at a step S52. The filter rotation monitoring section 112b makes this determination on the origin slit 14k on the basis of a signal generated by a slit width counter (not shown) provided therein. The slit width counter (not shown) generates an integral signal of the signal received from the sensor 16 as shown in FIG. 22. The ON-state period of the signal output from the sensor 16 upon detection of the origin slit 14k is longer than the ON-state period of the signal output from the sensor 16 upon detection of any normal slit 14l due to the width of the origin slit 14k larger than those of the remaining normal slits 14l. When the sensor 16 has detected the origin slit 14k, therefore, the integral signal generated by the slit width counter (not shown) of the filter rotation monitoring section 112b rises up to a level higher than those of integral signals output upon detection of the normal slits 14l. Thus, the filter rotation monitoring section 112b sets a prescribed threshold between the levels of rise of the integral signals output upon detection of the origin slit 14k and the normal slits 14l, for determining that the slit detected by the sensor 16 is the origin slit 14k when the corresponding integral signal reaches the prescribed threshold while determining that the slit detected by the sensor 16 is not the origin slit 14k (but any of the normal slits 14l) when the corresponding integral signal does not reach the prescribed threshold.

When determining that the slit detected by the sensor 16 is not the origin slit 14*k* at the step S52 in FIG. 21, the filter rotation monitoring section 112*b* returns to the step S51. When determining that the slit detected by the sensor 16 is the origin slit 14*k*, on the other hand, the filter rotation monitoring section 112*b* stores the time T1 when the sensor 16 has detected the origin slit 14*k* at a step S53. At a step S54, the filter rotation monitoring section 112*b* determines whether or not the sensor 16 has detected another slit similarly to the aforementioned step S51. When determining that the sensor 16 has detected no slit at the step S54, the filter rotation monitoring section 112*b* repetitively makes the determination at the step S54. When determining that the sensor 16 has detected another slit at the step S54, on the other hand, the filter rotation monitoring section 112*b* determines whether or not the slit detected by the sensor 16 is the origin slit 14*k*, similarly to the aforementioned step S52.

When determining that the slit detected by the sensor 16 is not the origin slit 14*k*, the filter rotation monitoring section 112*b* returns to the step S54. When determining that the slit detected by the sensor 16 is the origin slit 14*k* at the step S55, on the other hand, the filter rotation monitoring section 112*b* stores the time T(n) when the sensor 16 has detected the origin slit 14*k* at a step S56. Symbol n represents the frequency of detection of the origin slit 14*k*. Therefore, the sensor 16 has detected the origin slit 14*k* twice, and hence n=2 in this case.

At a step S57, the filter rotation monitoring section 112*b* calculates T(n)−T(n −1), i.e., T2−T1 since n=2. In other words, the filter rotation monitoring section 112*b* calculates the time interval between the first and second detection times T1 and T2 for the origin slit 14*k* at the step S57. At a step S58, the filter rotation monitoring section 112*b* determines whether or not the time interval T2−T1 calculated at the step S57 is in the range of a prescribed time interval previously set as necessary for single rotation of the filter section 14. When determining that the time interval T2−T1 is not in the range of the prescribed time interval at the step S58, the filter rotation monitoring section 112*b* outputs error information indicating that the rotation of the filter section 14 is abnormal to the controller status register 112*j* through the controller 112*a* at a step S59. At this time, rotation of the filter section 14 is stopped. The controller status register 112*j* temporarily stores the error information. Then, the controller status register 112*j* transmits the error information stored therein to the PC body 3*b* through the local bus interface 112*k* and the interface 116. Then, the PC body 3*b* displays an error message indicating that the rotation of the filter section 14 is abnormal on the display section 3*c* of the information processing terminal 3*a*.

When it is determined that the time interval T2−T1 is in the range of the prescribed time interval at the step S58, on the other hand, it is determined whether or not the control section 112 has instructed a stop of rotation of the filter plate 14 at a step S60. When determining that no stop of rotation of the filter section 14 has been instructed at the step S60, the filter rotation monitoring section 112*b* returns to the step S54. When determining that a stop of rotation of the filter section 14 has been instructed at the step S60, on the other hand, the filter rotation monitoring section 112*b* ends the monitoring operation on the rotation of the filter section 14. The filter rotation monitoring section 112*b* repeats the series of steps S54 to S60 until determining that the control section 112 has instructed a stop of rotation of the filter section 14 at the step S60.

An operation of monitoring the time interval for detecting two adjacent slits (the origin slit 14*k* or the normal slit(s) 14*l*) in the monitoring on the rotation of the filter section 14 with the control section 112 is now described with reference to FIGS. 2, 5, 9, 21 and 23.

Figure 23:
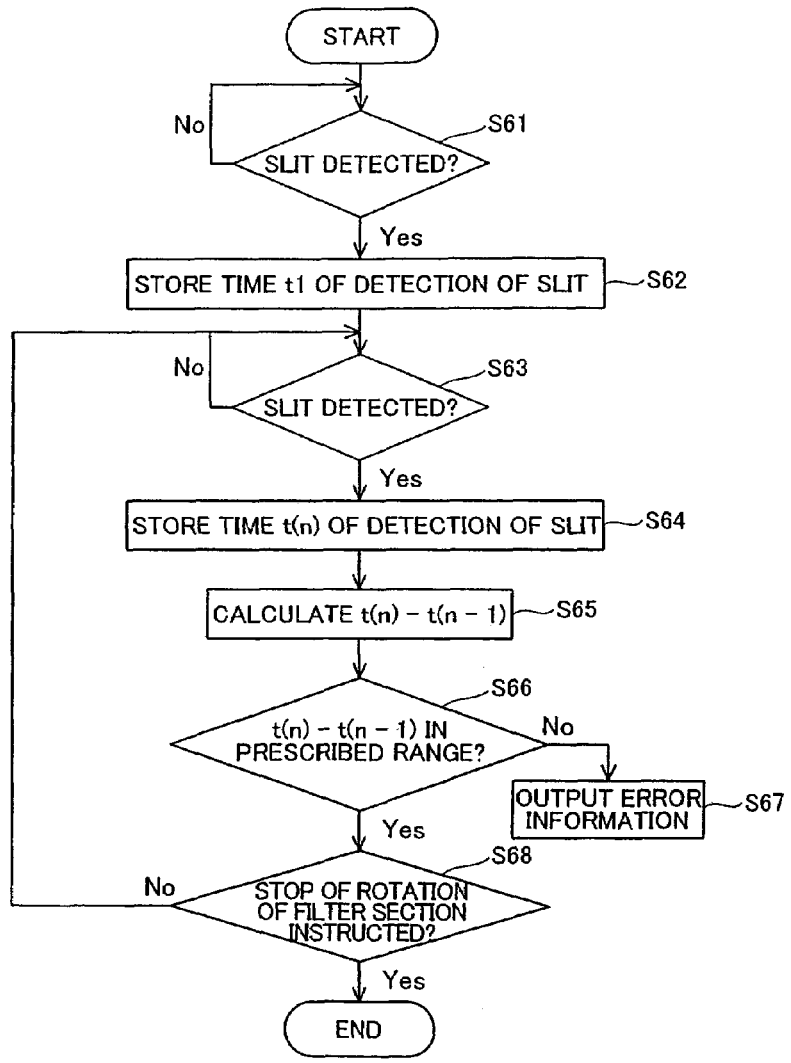
[FIG. 23] A flow chart showing processing of monitoring a time interval for detecting a pair of adjacent slits (the origin slit or normal slit(s)) in the processing of monitoring rotation of the filter section with the control section according to the first embodiment of the present invention.

At a step S61 in FIG. 23, the filter rotation monitoring section 112*b* of the control section 112 (see FIG. 9) determines whether or not the sensor 16 has detected passage of any slit (the origin slit 14*k* (see FIG. 5) or any of the normal slits 14*l*) on the basis of the corresponding signal from the sensor 16, similarly to the step S51 shown in FIG. 21. When determining that the sensor 16 (see FIG. 9) has detected no slit at the step S61, the step S61 is repeated. When determining that the sensor 16 has detected passage of any slit, on the other hand, the filter rotation monitoring section 112*b* stores the time t1 when the sensor 16 has detected this slit at a step S62.

At a step S63, it is determined whether or not the sensor 16 has detected passage of another slit, similarly to the aforementioned step S61. When determining that the sensor 16 has detected passage of no slit at the step S63, the step S63 is repeated. When it is determined that the sensor 16 has detected passage of another slit at the step S63, on the other hand, the filter rotation monitoring section 112*b* stores the time t(n) when the sensor 16 has detected this slit at a step S64. Symbol n represents the frequency of detection of slits by the sensor 16. Therefore, the sensor 16 has detected the slits twice, and hence n=2 in this case.

At a step S65, the filter rotation monitoring section 112*b* calculates t(n)−t(n −1), i.e., t2−t1 since n=2. In other words, the filter rotation monitoring section 112*b* calculates the time interval between the first and second slit detection times t1 and t2 at the step S65. At a step S66, the filter rotation monitoring section 112*b* determines whether or not the time interval t2−t1 calculated at the step S65 is in the range of a prescribed time interval previously set as that between the times for detecting two adjacent slits respectively. This time interval is either a first time interval required for normal passage of the optical filter 14*e* following passage of the optical filter 14*f* or a second time interval required for normal passage of the optical filter 14*f* following passage of the optical filter 14*b*.

When determining that the time interval t2−t1 is neither in the range of the aforementioned first time interval nor in the range of the aforementioned second time interval at the step S66, the filter rotation monitoring section 112*b* outputs error information indicating that the rotation of the filter section 14 is abnormal to the controller status register 112*j* through the controller 112*a* at a step S67. At this time, rotation of the filter section 14 is stopped. The controller status register 112*j* temporarily stores the error information. Then, the controller status register 112*j* transmits the error information stored therein to the PC body 3*b* through the local bus interface 112*k* and the interface 116. Then, the PC body 3*b* displays an error message indicating that the rotation of the filter section 14 is abnormal on the display section 3*c* of the information processing terminal 3*a* (see FIG. 2).

When determining that the time interval t2−t1 is in the range of the prescribed time interval at the step S66, on the other hand, the filter rotation monitoring section 112*b* determines whether or not a stop of rotation of the filter section 14 has been instructed at a step S68. When determining that no stop of rotation of the filter section 14 has been instructed at the step S68, the filter rotation monitoring section 112*b* returns to the step S63. When determining that a stop of rotation of the filter section 14 has been instructed at the step S68, on the other hand, the filter rotation monitoring section 112*b* ends the monitoring operation on the rotation of the filter section 14. The filter rotation monitoring section 112*b* repeats the series of steps S61 to S68 until determining that a stop of rotation of the filter section 14 has been instructed at the step S68.

An operation of monitoring the number of the normal slits 14*l* detected while the two origin slits 14*k* are detected in the monitoring on the rotation of the filter section 14 with the control section 112 according to the first embodiment is described with reference to FIGS. 2, 5, 9, 21 and 24.

Figure 24:
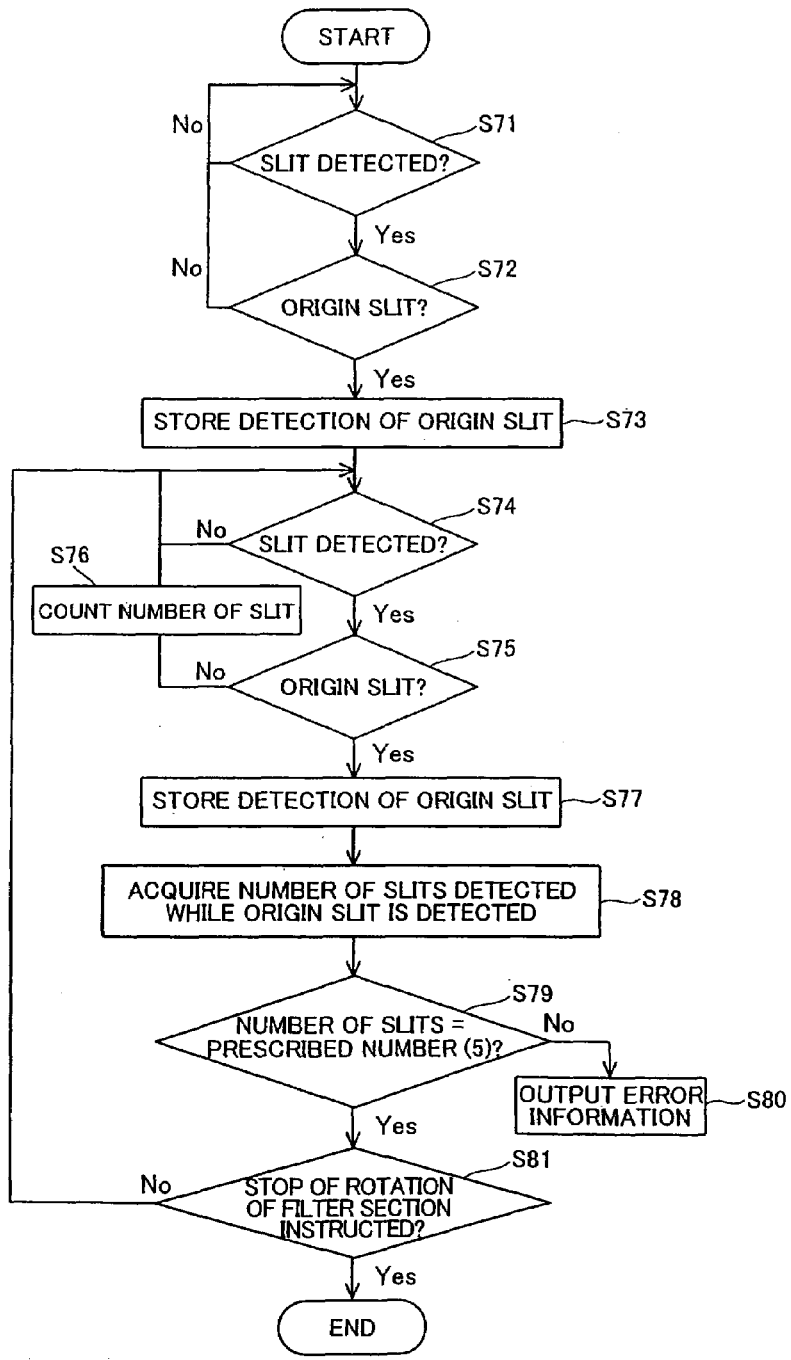
[FIG. 24] A flow chart showing processing of monitoring the number of normal slits detected while the two origin slits are detected in the processing of monitoring rotation of the filter section with the control section according to the first embodiment of the present invention.

At a step S71 shown in FIG. 24, the filter rotation monitoring section 112*b* of the control section 112 (see FIG. 9) determines whether or not the sensor 16 has detected any slit of the rotating filter section 14 (see FIG. 15) on the basis of the corresponding signal from the sensor 16, similarly to the step S51 shown in FIG. 21. When determining that the sensor 16 (see FIG. 9) has detected no slit at the step S71, the filter rotation monitoring section 112*b* repeats the step S71.

When determining that the sensor 16 has detected any slit at the step S71, on the other hand, the filter rotation monitoring section 112*b* determines whether or not the slit detected by the sensor 16 is the origin slit 14*k* at a step S72, similarly to the step S52 shown in FIG. 21. When determining that the detected slit is not the origin slit 14*k* at the step S72, the filter rotation monitoring section 112*b* returns to the step S71. When determining that the detected slit is the origin slit 14*k* at the step S72, on the other hand, the filter rotation monitoring section 112*b* stores the information indicating that the sensor 16 has detected the origin slit 14*k* at a step S73.

At a step S74, it is determined whether or not the sensor 16 has detected another slit, similarly to the aforementioned step S71. When determining that the sensor 16 has detected no slit at the step S74, the step S74 is repeated. When it is determined that the sensor 16 has detected another slit at the step S74, on the other hand, it is determined whether or not the detected slit is the origin slit 14*k* at a step S75, similarly to the aforementioned step S72. When it is determined that the detected slit is not the origin slit 14*k* (but any of the normal slits 14*l*) at the step S75, the number of the slit (normal slit 14*l*) detected at the step S75 is counted at a step S76. Thereafter the filter rotation monitoring section 112*b* returns to the step S74.

When determining that the detected slit is the origin slit 14*k* at the step S75, on the other hand, the filter rotation monitoring section 112*b* stores the information indicating that the sensor 16 has detected the origin slit 14*k* at a step S77. At a step S78, the filter rotation monitoring section 112*b* acquires the number of the normal slits 14*l* counted at the step S76 as that of the normal slits 14*l* detected while the two origin slits 14*k* have been detected. At a step S79, the filter rotation monitoring section 112*b* determines whether or not the number of the normal slits 14*l* acquired at the step S78 is a prescribed number (5). When determining that the acquired number of the normal slits 14*l* is not the prescribed number (5) at the step S79, the filter rotation monitoring section 112*b* outputs error information indicating that the rotation of the filter section 14 is abnormal to the controller status register 112*j* through the controller 112*a* at a step S80. At this time, rotation of the filter section 14 is stopped. The controller status register 112*j* temporarily stores the error information. Then, the controller status register 112*j* transmits the error information stored therein to the PC body 3*b* through the local bus interface 112*k* and the interface 116. Then, the PC body 3*b* displays an error message indicating that the rotation of the filter section 14 is abnormal on the display section 3*c* of the information processing terminal 3*a* (see FIG. 2).

When determining that the acquired number of the normal slits 14*l* is the prescribed number (5) at the step S79, on the other hand, the filter rotation monitoring section 112*b* determines whether or not a stop of rotation of the filter section 14 has been instructed at a step S81. When determining that no stop of rotation of the filter section 14 has been instructed at the step S81, the filter rotation monitoring section 112*b* returns to the step S74. When determining that a stop of rotation of the filter section 14 has been instructed at the step S 81, on the other hand, the filter rotation monitoring section 112*b* ends the monitoring operation on the rotation of the filter section 14. The filter rotation monitoring section 112*b* repeats the series of steps S74 to S81 until determining that a stop of rotation of the filter section 14 has been instructed at the step S81.

According to the first embodiment, as hereinabove described, the lamp unit 5 successively switching the five optical filters 14*b* to 14*f* having different light transmission characteristics arranged on the path of the light from the halogen lamp 11 by rotating the filter section 14 having the optical filters 14*b* to 14*f* at the substantially constant speed and successively irradiating the measurement samples with the lights having different wavelength characteristics is provided, whereby the optical filters 14*b* to 14*f* can be switched frequently in a short period of 100 msec. dissimilarly to a case of applying a light after rotation of the filter section 14 is stopped once every time the wavelength of the applied light is switched. Further, control of the rotation of the filter section 14 in a case of switching the optical filters 14*b* to 14*f* can be inhibited from complication.

According to the first embodiment, as hereinabove described, the filter section 14 having the five optical filters 14*b* to 14*f* rotates at the substantially constant speed so that the optical filters 14*b* to 14*f* may not be stopped on the path of the light from the halogen lamp 11, and hence no positioning of the optical filters 14*b* to 14*f* with respect to the path of the light from the halogen lamp 11 is required. The optical filters 14*b* to 14*f* may not be stopped on the path of the light from the halogen lamp 11, and hence no expensive motor having a high positioning accuracy is required to be employed. Thus, the analyzer at a low price can be provided.

According to the first embodiment, as hereinabove described, the photoelectric conversion elements 84*a* detect the lights obtained by irradiating the analyzing objects with the lights from the lamp unit 5 and output the signals corresponding to the detected lights and the PC body 3*b* analyzes the characteristics of the analyzing objects on the basis of the signals output from the photoelectric conversion elements 84*a*, whereby the photoelectric conversion elements 84*a* and the PC body 3*b* can easily analyzes the characteristics of the analyzing objects on the basis of the lights obtained by irradiating the analyzing objects with the lights from the lamp unit 5.

According to the first embodiment, as hereinabove described, the control section 112 selectively acquires, from the photoelectric conversion elements 84*a*, specific signals corresponding to the lights detected by the photoelectric conversion elements 84*a* when the lamp unit 5 irradiates the analyzing objects with the lights transmitted through the optical filters 14*b* to 14*f*, and the PC body 3*b* analyzes the characteristics of the analyzing objects on the basis of the specific signals acquired by the control section 112, whereby the characteristics of the analyzing objects can be easily analyzed on the basis of the specific signals corresponding to the lights detected by the photoelectric conversion elements 84*a* when the lamp unit 5 irradiates the analyzing objects with the lights transmitted through the optical filters 14*b* to 14*f*.

According to the first embodiment, as hereinabove described, the control section 112 detects the timing of arrangement of the optical filters 14*b* to 14*f* on the path of the light from the halogen lamp 11 and starts acquiring the specific signals on the basis of the timing, whereby the lights corresponding to the lights detected through the analyzing objects when the optical filters 14b to 14f are arranged on the path from the halogen lamp 11 can be reliably acquired.

According to the first embodiment, as hereinabove described, the control section 112 starts acquiring the specific signals after the lapse of the prescribed time from the point of time when the sensor 16 detects any slit so that the time from detection of the slit is measured, whereby the timing of arrangement of the optical filters 14b to 14f on the path of the light from the halogen lamp 111 can be correctly detected.

According to the first embodiment, as hereinabove described, the control section 112 detects the timing of arrangement of the optical filters 14b to 14f on the path of the light from the halogen lamp 11 on the basis of the reference signal output from the reference light photoelectric conversion element 84b, whereby change in the quantities of the lights due to the arrangement of the optical filters 14b to 14f on the path of the light from the halogen lamp 11 definitely appears as compared with a case of employing a signal corresponding to a light applied through an analyzing object and hence the timing of arrangement of the optical filters 14b to 14f on the path of the light from the halogen lamp 11 can be further correctly detected.

According to the first embodiment, as hereinabove described, the PC body 3b selects the optical information suitable for analysis from among 10 types of optical information having different wavelength characteristics and different amplification rates in accordance with the characteristics of the specimens and analyzes the characteristics of the analyzing objects, whereby the PC body 3b can further improve analysis accuracy of the characteristics of the specimens.

According to the first embodiment, as hereinabove described, the PC body 3b creates the time-series data on the basis of the specific signals acquired by the control section 112 and analyzes the characteristics of the analyzing objects on the basis of the created time-series data, whereby the analytic system 1 can easily analyze the characteristics of the analyzing objects on the basis of the time-series data.

According to the first embodiment, as hereinabove described, the PC body 3b acquires the prescribed partial time-series data at each prescribed time interval from the specific signals stored in the logger memory 112h and creates the time-series data by combining the acquired partial time-series data, whereby the PC body 3b can easily create the time-series data.

According to the first embodiment, as hereinabove described, rotation of the filter section 14 is controlled on the basis of results of monitoring the rotation of the filter section 14 with the filter rotation monitoring section 112b, whereby normal rotation of the filter section 14 can be kept.

According to the first embodiment, as hereinabove described, the filter rotation monitoring section 112b monitors whether or not the filter section 14 normally rotates on the basis of the detection results of the sensor 16, whereby it can be easily monitored whether or not the filter section 14 normally rotates.

According to the first embodiment, as hereinabove described, the PC body 3b analyzes the time from the point of the time when the cuvettes 152 (see FIG. 1) storing the measurement samples have been received in the receiving holes 81a of the second optical information acquisition section 80 after the reagents are mixed into the analyzing objects with the reagent injection arms 50 to the point of the time when the analyzing objects are changed into the prescribed coagulation states, whereby a large quantity of the optical information of the analyzing objects can be continuously acquired within a prescribed time with the lights transmitted through the optical filters 14b to 14f rotating at the substantially constant speed, and hence the coagulation times of the analyzing objects can be correctly analyzed on the basis of the large quantity of optical information.

Second Embodiment

An operation of an analytic system according to a second embodiment of the present invention is now described. The analytic system according to the second embodiment are similar in structure to that of the analytic system 1 according to the aforementioned first embodiment, and hence redundant description thereof is omitted. In the analytic system according to the second embodiment, a control section 112 acquires data not with a differential signal of a reference signal but with detection signals of slits of the filter section 14 dissimilarly to the analytic system 1 according to the aforementioned first embodiment.

Figure 26:
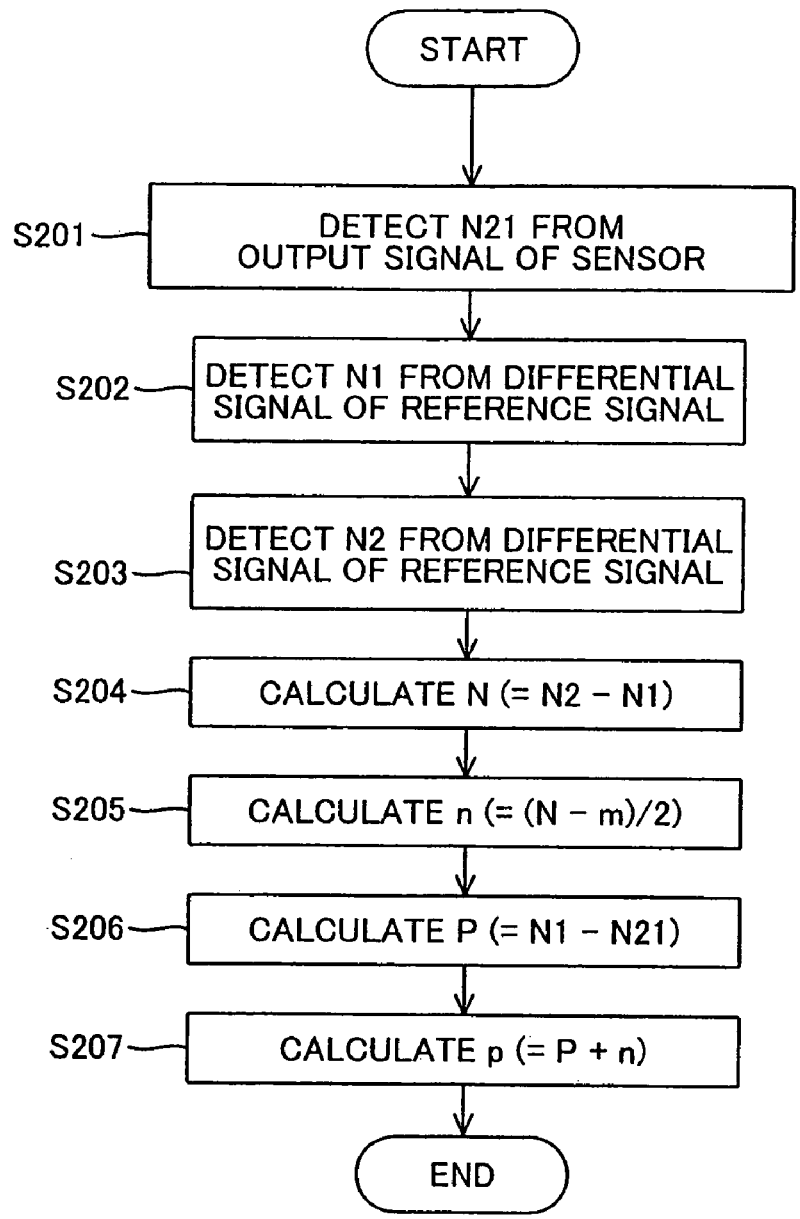
[FIG. 26] A flow chart showing processing of calculating p clocks with a control section according to a second embodiment of the present invention.
Figure 27:
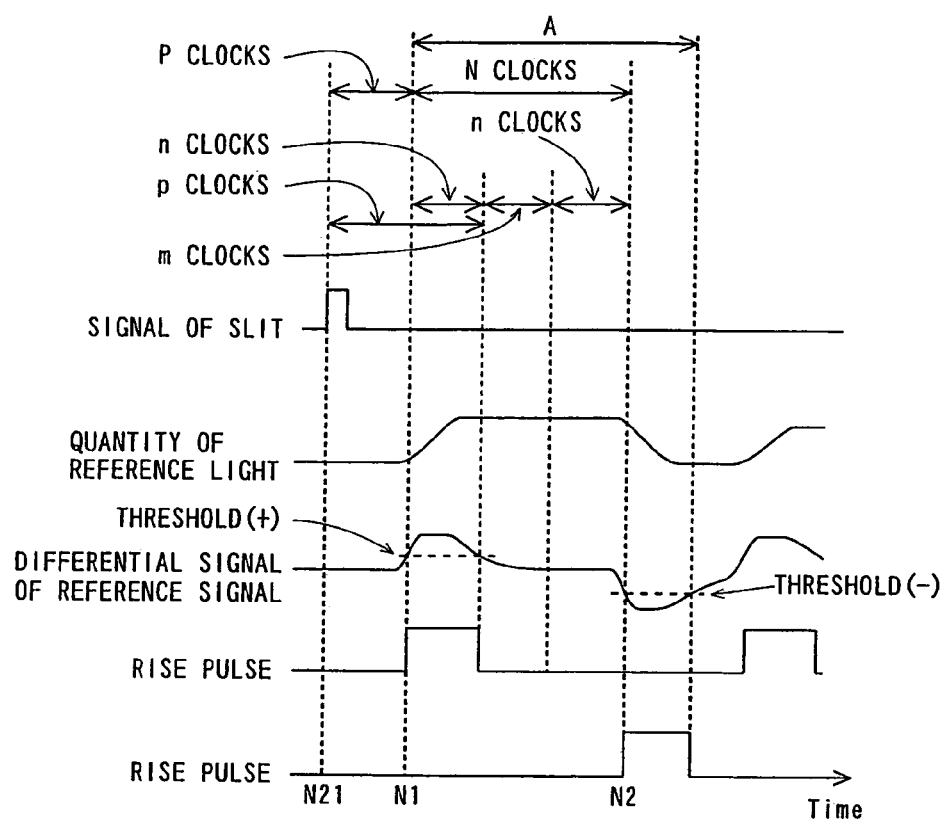
[FIG. 27] A waveform diagram showing changes in a slit detection signal and the quantity of a reference light and a differential signal of a reference signal employed in the method of calculating p clocks shown in FIG. 26.

Initialization of the analytic system according to the second embodiment is described. The analytic system according to the second embodiment calculates a clock number p of a lapse from slit detection to start of data acquisition as described below. FIG. 26 is a flow chart showing calculation of p clocks of the control section according to the second embodiment. The control section 112 (see FIG. 9) detects a clock number N21 at a point of time when a sensor 16 detects any slit on the basis of a signal received from the sensor 16 (step S201) in a state where the filter section 14 rotates. The control section 112 detects a clock number N1 at a point of time when the differential signal of the reference signal reaches a prescribed negative threshold (+) (step S202), detects a clock number (N2) at a point of time when the differential signal of the reference signal reaches a prescribed negative threshold (−) (step S203), calculates the number of clocks (N clocks) counted between the clock numbers N1 and N2 according to a formula N=N2−N1 (step S204), and calculates the n clocks from the leading edge of the reference signal to the timing for starting acquiring the signals corresponding to the lights transmitted through the measurement samples according to a formula n=(N−m)/2 (step S205), similarly to the steps S11 to S14 according to the aforementioned first embodiment. At a step S206, the control section 112 calculates the number of clocks (P clocks) from the slit detection to the leading edge of the reference signal according to a formula P=(N1−N21), and at a step S207, the control section 112 calculates the number of clocks (p clocks) for deciding the timing for starting acquiring the signals corresponding to the lights transmitted through the measurement samples according to a formula p=P+n. Thus, according to the second embodiment, the control section 112 calculates the timing for starting acquiring the signals corresponding to the transmitted lights with the slits provided in the filter section 14. As understood from FIG. 27, the control section 112 can acquire signals in a period where the quantities of the lights applied from the lamp unit 5 are stable by acquiring the signals corresponding to the lights transmitted through the measurement samples from the detection section 82 for the period of m clocks with the multiplexers 111a after p clocks calculated in the aforementioned manner from the clock N21.

Data acquisition with the control section 112 according to the second embodiment is now described. The PC body 3b instructs analysis, in order to start this data acquisition.

Figure 28:
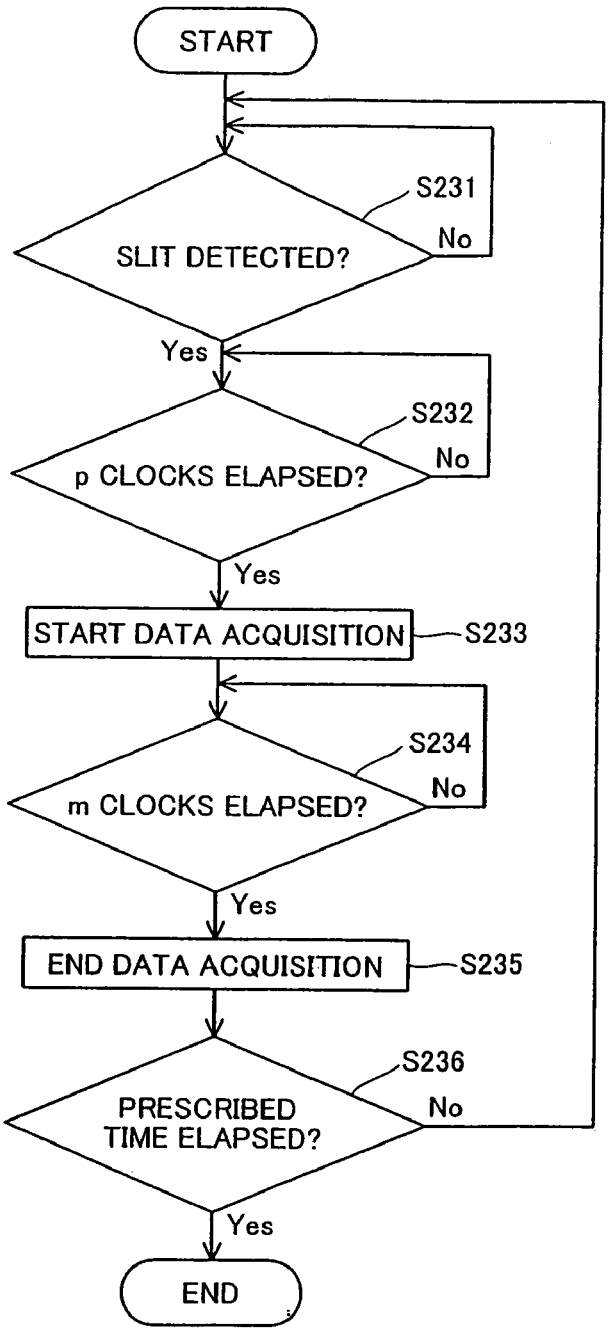
[FIG. 28] A flow chart for illustrating a method of data acquisition with the control section according to the second embodiment of the present invention.

FIG. 28 is a flow chart showing an operation of data acquisition of the control section according to the second embodiment. At a step S231 shown in FIG. 28, the control section 112 determines whether or not the sensor 16 has detected any slit on the basis of the signal received from the sensor 16. When detecting the slit, the control section 112 waits for a lapse of p clocks calculated in the initialization from the slit detection at a step S232. Processing at subsequent S233 to S236 are similar to that at the steps 33 to 36 according to the aforementioned first embodiment, and hence redundant description thereof is omitted.

The remaining operations of the analytic system according to the second embodiment are similar to those of the analytic system 1 according to the aforementioned first embodiment, and hence redundant description thereof is omitted.

The effects of the second embodiment are similar to those of the aforementioned first embodiment.

The embodiment disclosed this time must be considered as illustrative in all points and not restrictive. The range of the present invention is shown not by the above description of the embodiment but by the scope of claim for patent, and all modifications within the meaning and range equivalent to the scope of claim for patent are included.

For example, while the data output from the detection section and the signal processing section is temporarily stored in the logger memory of the control section so that the PC body successively acquires the partial time-series data of the prescribed period from the data stored in the logger memory in each of the aforementioned first and second embodiments, the present invention is not restricted to this but the data may alternatively directly be output from the detection section or the signal processing section to the PC body without temporarily storing the data in the logger memory.

While the control section calculates the timing ($\underline{n}$ clocks) for starting signal acquisition on the basis of the differential signal of the reference signal and starts acquiring data upon a lapse of the calculated $\underline{n}$ clocks after the differential signal of the reference signal reaches the prescribed threshold in the aforementioned first embodiment, the present invention is not restricted to this but the control section may alternatively start data acquisition at previously set timing.

While the control section starts data acquisition upon a lapse of $\underline{n}$ clocks from the leading edge of the differential signal of the reference signal corresponding to the reference light in the aforementioned first embodiment, the present invention is not restricted to this but the control section may alternatively start data acquisition upon a lapse of a prescribed period from the time when the sensor has detected any slit.

While the p clocks are calculated by the initialization employing the reference signal in the aforementioned second embodiment, the present invention is not restricted to this but a fixed value may alternatively previously be provided as p clocks or a user may freely set p clocks, for example.

Figure 29:
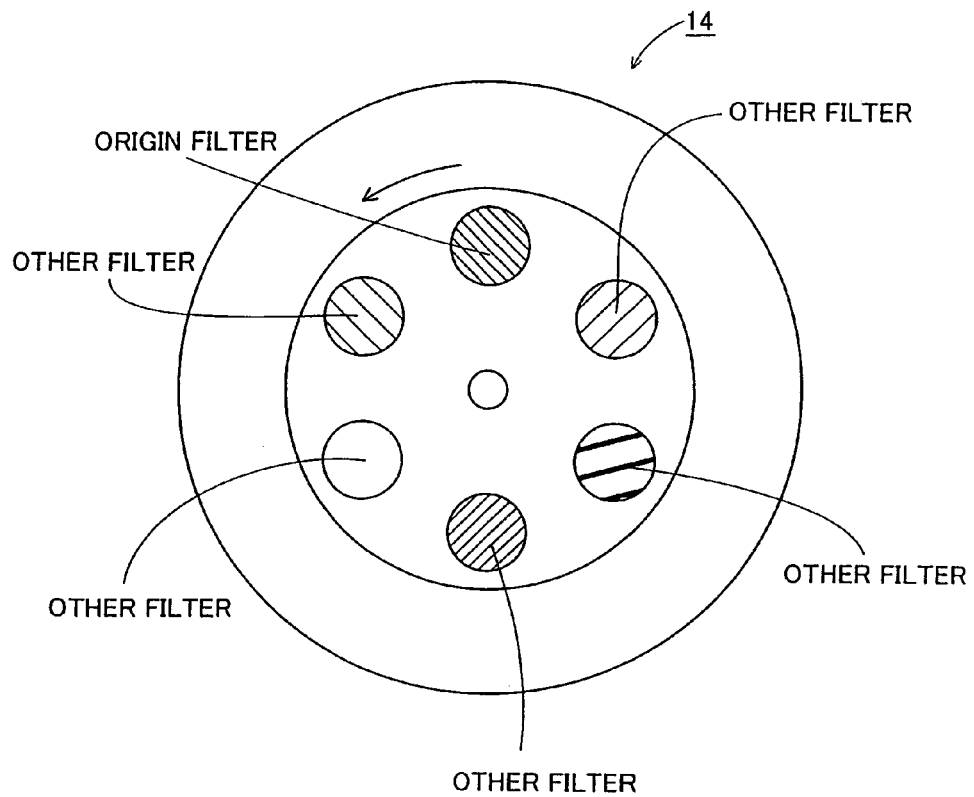
[FIG. 29] A schematic diagram of a rotating filter illustrating a case of monitoring rotation of a filter section with a reference signal.
Figure 30:
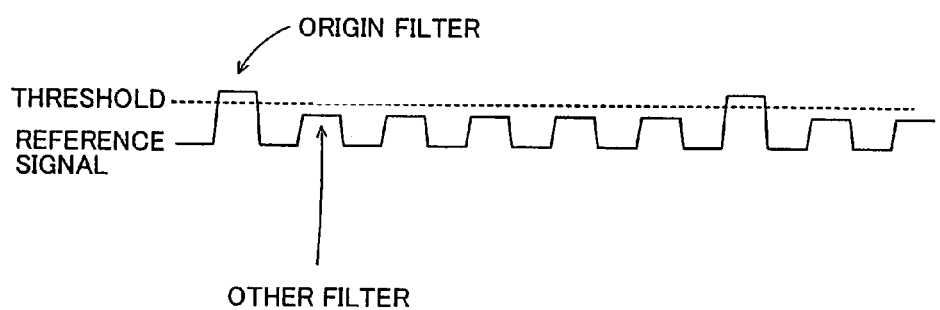
[FIG. 30] A schematic diagram of the reference signal illustrating a case of monitoring rotation of the filter section with the reference signal.

While rotation of the filter section 14 is monitored with the slits provided in the filter section 14 in the aforementioned first embodiment, the present invention is not restricted to this but the rotation of the filter section 14 may alternatively be monitored with a reference signal. For example, when the quantity of reference light transmitted through a single filter (hereinafter referred to as an origin filter) is different from the quantity of reference light transmitted through any one of other filters (hereinafter referred to as other filters) other than the origin filter as shown in FIG. 29, rotation of the filter section 14 may be alternatively monitored by monitoring the level of the reference signal for specifying passage of the origin filter (with a threshold smaller than the level of the reference signal only at the time of the passage of the origin filter and larger than the level of the reference signal at the time of the passage of any other filter as shown in FIG. 30, for example), and measuring a time elapsed from the passage of the origin filter to the next passage of the origin filter.

While the present invention is applied to the analyzer performing coagulation measurement in each of the aforementioned first and second embodiments, the present invention is not restricted to this but may also be applied to an analyzer (analytic system) performing measurement, other than coagulation measurement, requiring employment of a plurality of lights having different wavelength characteristics. For example, the present invention may be applied to a biochemical analyzer (analytic system).

While the information processing terminal is provided independently of the body of the analyzer in each the aforementioned first and second embodiments, the present invention is not restricted to this but the information processing terminal and the body of the analyzer may alternatively be integrated with each other.

While the analyzer is rendered extendable with the extension analyzer for treating a large number of specimens in each of the aforementioned first and second embodiments, the present invention is not restricted to this but the analyzer may alternatively be rendered unextendable with any extension analyzer.

While the multiplexers selecting the signals one by one from the plurality of analog signals output from the plurality of photoelectric conversion elements and successively outputting the same to the offset circuits are employed in each of the aforementioned first and second embodiment, the present invention is not restricted to this but an analog signal selector simultaneously selecting at least two signals from the plurality of analog signals output from the plurality of photoelectric conversion elements may alternatively be employed.

What is claimed is:

1. An analyzer comprising:
a light irradiation device including a light source and a rotatable filter section comprising a plurality of optical filters with different light transmission characteristics respectively and irradiating an analyzing object with lights transmitted through said optical filters during rotation of said filter section while successively switching said optical filters arranged on a light path from said light source by rotating said filter section, wherein said plurality of optical filters are arranged on said rotatable filter section such that angles between the light path from said light source and surfaces of said optical filters do not change by rotation of said rotatable filter section; and
analytic processor analyzing characteristics of said analyzing object on the basis of optical information obtained from said analyzing object irradiated with the lights by said light irradiation device during the rotation of said filter section.

2. The analyzer according to claim 1, further comprising a photodetection section detecting lights obtained by irradiating said analyzing object with the lights from said light irradiation device and outputting signals corresponding to the detected lights, wherein
said analytic processor analyzes characteristics of said analyzing object on the basis of the signals output from said photodetection section.

3. The analyzer according to claim 2, further comprising signal acquirer acquiring specific signals corresponding to lights detected with said photodetection section when said light irradiation device irradiates said analyzing object with the lights transmitted through said optical filters from said photodetection section, wherein said analytic processor analyzes characteristics of said analyzing object on the basis of the specific signals acquired with said signal acquirer.

4. The analyzer according to claim 3, wherein
said signal acquirer detects timing of arrangement of said optical filters on the light path from said light source and starts acquiring said specific signals on the basis of said timing.

5. The analyzer according to claim 4,
wherein said filter section comprises a plurality of identifiers provided on prescribed positions with respect to said plurality of optical filters respectively;
wherein said analyzer further comprises an identifier detection section detecting said plurality of identifiers; and
wherein said signal acquirer starts acquiring said specific signals after a lapse of a prescribed time from a point of time when said identifier detection section detects each of the identifiers.

6. The analyzer according to claim 4, further comprising a reference light detection section detecting a reference light emitted from said light irradiation device without through said analyzing object and outputting a reference signal corresponding to detected said reference light, wherein
said signal acquirer detects said timing of the arrangement of said optical filters on the light path from said light source on the basis of said reference signal output from said reference light detection section.

7. The analyzer according to claim 4, wherein
said signal acquirer detects said timing of the arrangement of said optical filters on the light path from said light source on the basis of the signals output from said photodetection section.

8. The analyzer according to claim 3, wherein
the specific signals acquired with said signal acquirer includes a first signal acquired with said signal acquirer when said analyzing object is irradiated with a light transmitted through a first optical filter from said light irradiation device and a second signal acquired with said signal acquirer when said analyzing object is irradiated with a light transmitted through a second optical filter from said light irradiation device, and
said analytic processor analyzes characteristics of said analyzing object by selecting either said first signal or said second signal in accordance with characteristics of a specimen.

9. The analyzer according to claim 3, wherein
said analytic processor creates time-series data on the basis of the specific signals acquired with said signal acquirer and analyzes characteristics of said analyzing object on the basis of created said time-series data.

10. The analyzer according to claim 9, further comprising a signal storage section storing the specific signals acquired with said signal acquirer, wherein
said analytic processor acquires prescribed partial time-series data at each prescribed time interval from the specific signals stored in the said signal storage section and creates said time-series data by combining acquired said partial time-series data.

11. The analyzer according to claim 2, wherein
said light irradiation device disposes said each optical filters on said light path plural times during irradiating one analyzing object; and
said analytic processor analyzes characteristics of said one analyzing object by combining at least first signal output from said photodetection section when a specific filter among said optical filters is disposed on said light path and said second signal output from said photodetection section when said specific filter is disposed on said light path at different timing from that of said first signal.

12. The analyzer according to claim 1, further comprising a monitor monitoring whether or not said filter section normally rotates.

13. The analyzer according to claim 12, wherein said filter section has a plurality of openings arranged at a prescribed interval along a direction of rotation of said filter section, further comprising
a sensor detecting passage of said openings following the rotation of said filter section, wherein
said monitor monitors whether or not said filter section normally rotates on the basis of detection results of said sensor.

14. The analyzer according to claim 13, wherein
said plurality of openings include a single initial opening and non-initial openings having different shapes from said initial opening, and
said monitor monitors whether or not said filter section normally rotates on the basis of detection results of said initial opening and said non-initial openings with said sensor.

15. The analyzer according to claim 1, further comprising
a reagent mixing section mixing a reagent into said analyzing object, wherein
said analytic processor analyzes a time required for said analyzing object to reach a prescribed state from prescribed timing after said reagent is mixed into said analyzing object by said reagent mixing section.

16. The analyzer according to claim 15, wherein
said prescribed state is a state where said analyzing object has reached a prescribed coagulation state.

17. The analyzer according to claim 1, wherein
said rotatable filter section comprises a palate having a plurality of holes; and
said plurality of optical filters are arranged on said holes.

18. An analyzer comprising:
a light source;
a rotatable filter section;
a plurality of optical filters, arranged on said rotatable filter section, having different light transmission characteristics respectively;
filter rotator rotating said rotatable filter section such that said plurality of optical filters successively pass through a light path from said light source at a constant speed; and
analytic processor analyzing characteristics of said analyzing object on the basis of optical information obtained by irradiating an analyzing object with lights transmitted through said optical filters from the light source, wherein
said plurality of optical filters are arranged on said rotatable filter section such that angles between said light path from said light source and surfaces of said optical filters do not change by rotation of said rotatable filter section.

19. The analyzer according to claim 18, further comprising a photodetection section detecting lights obtained by irradiating said analyzing object with the lights from said light source and outputting signals corresponding to the detected lights, wherein
said analytic processor analyzes characteristics of said analyzing object on the basis of the signals output from said photodetection section.

20. The analyzer according to claim 19, further comprising signal acquirer acquiring specific signals corresponding to lights detected with said photodetection section when said analyzing object is irradiated with the lights transmitted through said optical filters from said photodetection section, wherein said analytic processor analyzes characteristics of said analyzing object on the basis of the specific signals acquired with said signal acquirer.

21. The analyzer according to claim 20, wherein
said signal acquirer detects timing of arrangement of said optical filters on the light path from said light source and starts acquiring said specific signals on the basis of said timing.

22. An analyzer comprising:
a light irradiation device including a light source and a rotatable filter section comprising a plurality of optical filters with different light transmission characteristics respectively and irradiating an analyzing object with lights transmitted through said optical filters while successively switching said optical filters arranged on a light path from said light source at a time interval of at most one second by rotating said filter section, wherein said plurality of optical filters are arranged on said rotatable filter section such that angles between the light path from said light source and surfaces of said optical filters do not change by rotation of said rotatable filter section; and analytic processor analyzing characteristics of said analyzing object on the basis of optical information obtained from said analyzing object irradiated with said lights by said light irradiation device.

* * * * *